US008809013B2

(12) United States Patent
Heindl et al.

(10) Patent No.: US 8,809,013 B2
(45) Date of Patent: Aug. 19, 2014

(54) STABLE NAD/NADH DERIVATIVES

(75) Inventors: Dieter Heindl, Paehl (DE); Joachim Hoenes, Zwingenberg (DE); Carina Horn, Biblis (DE); Claudia Gaessler-Dietsche, Schriesheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 419 days.

(21) Appl. No.: 12/020,244

(22) Filed: Jan. 25, 2008

(65) Prior Publication Data
US 2008/0213809 A1 Sep. 4, 2008

Related U.S. Application Data

(63) Continuation of application No. PCT/EP2006/007493, filed on Jul. 28, 2006.

(30) Foreign Application Priority Data

Jul. 28, 2005 (DE) .......................... 10 2005 035 461

(51) Int. Cl.
C12Q 1/32 (2006.01)
(52) U.S. Cl.
USPC ................................. 435/26; 435/4
(58) Field of Classification Search
USPC ...................................... 435/26, 4
See application file for complete search history.

(56) References Cited

U.S. PATENT DOCUMENTS 5,801,006 A  9/1998  Kaufman

FOREIGN PATENT DOCUMENTS

| CA | 2493918 A1 | 11/2003 |
| DE | 10221845 A1 | 11/2003 |
| JP | 43-007333 B | 4/1968 |
| JP | 53-107486 A | 9/1978 |
| JP | 2000-007696 A | 1/2000 |
| JP | 2001-526528 A | 12/2001 |
| WO | 98/33936 A1 | 8/1998 |
| WO | 01/49247 A2 | 7/2001 |
| WO | 01/94370 A1 | 12/2001 |

OTHER PUBLICATIONS

Slama et al. "Carbanicotinamide adenine dinucleotide: synthesis and enzymological properties of a carbocyclic analogue of oxidized nicotinamide adenine dinucleotide", Biochemistry, 1988, 27:183-193.*
Kiechle et al. "Blood glucose: measurement in the point-of-care setting", Laboratory Medicine, 2000, 31(5):276-282.*
Oppenheimer, Norman J., "The Pyrdine Nucleotide Coenzyms", Academic Press New York, London, Chapter 3, pp. 56-67, (1982).
Kaplan, Nathan O. et al., "Chemistry and properties of the 3 acetylpyridine analogue of diphosphopyridine nucleotide", The Journal of Biological Chemistry, 221, pp. 823-832, (1955).
Slama, James T. et al., "Inhibition of NAD Glycohydrolase and ADP-ribosyl Transferases by Carboncyclic Analogues of Oxidized Nicotinamide Adenine Dinucleotide", Biochemistry, 28, pp. 7688-7694, (1989).
Huryn, Donna M. et al., "Synthesis of ISO-DDA, Member of a novel class of Anti-HIV Agents", Tetrahedron Letters, vol. 30, No. 46, pp. 6259-6262, (1989).
Beres, J. et al, "Stereospecific Synthesis of (-)-Carbocyclic 2', 3'-Dideoxythymidine, a Potential Anti-Aids Agent", Tetrahedron Letters, vol. 29, No. 22, pp. 2681-2684, (1988).
XP-001085208. Anderson, Bruce M., "Analogs of Pyridine Nucleotide Coenzymes", Pyridine Nucleotide Coenzymes, pp. 91-133, (1982).
XP-002405611. Muller-Steffner, Helene et al, Photodependent Inhibition of Bovine Spleen NAD+ Glycohydrolase by 8-Azido Carbocyclic Analogs of NAD+, Biochemical and Biophysical Research Communications, 228, pp. 128-133, (1996).
XP-002405612. Sleath, Paul R. et al., "Pyridine Coenzyme Analogues. 3. Synthesis of Three NAD+ Analogues Containing a 2'-Deoxy-2'-substituted Nicotinamide Arabinofuranosyl Moiety", J. Org. Chem., 56, pp. 3608-3613, (1991).
XP-002405653. Slama, James T. et al., "Carbanicotinamide Adenine Dinucleotide: Synthesis and Enzymological Properties of a Carbocyclic Analogue of Oxidized Nicotinamide Adenine Dinucleotide", Biochemistry, 27, pp. 183-193, (1988).
XP008070860. Hutchinson, Brian F. et al., "Synthesis of carboncyclic NAD+ containing a methylenebisphosphonate linkage for investigation of ADP-ribosyl cyclase", Chem. Commun., pp. 2765-2766, (1996).
Kuchel, P.W., et al., "Direct observation of the NAD glycohydrolase reaction in human crythocytes using NMR spectroscopy", Experientia, 41, 1985, pp. 53-55.
Wall, Katherine A., et al., "Inibition of the intrinsic NAD+ glycohydrolase activity of CD38 by carhocyclic NAD analogues", Biochem. J., 335, 1998, pp. 631-636.
Research from Caplus and Medline for "adenin analog structure" dated Nov. 9, 2009, pp. 3-5.
Akasako et al., "High Resistance of *Escherichia coli* Ribonuclease HI Variant with Quintuple Thermostabilizing Mutations to Thermal Denaturation, Acid Denaturation, and Proteolytic Degradation", Biochemistry 1995, 34, pp. 8115-8122.
Brems, et al., "The Conformational Stability and Flexibility of Insulin with an Additional Intramolecular Cross-link", The Journal of Biological Chemistry 1991, vol. 266, No. 3, Jan. 25, pp. 1611-1615.
Hasegawa, et al., "Selected Mutations in a Mesophilic: Cytochrome c Confer the Stability of a Thermophilic Counterpart", The Journal of Biological Chemistry 2000. vol. 275, No. 48, pp. 37824-37828.
Hasegawa, et al., "Stabilization of *Pseudomonas aeruginosa* Cytochrome c551 by Systematic Amino Acid Substitutions Based on the Structure of Thermophilic Hyrdrogenobacter thermophilus Cytochronie c522", The Journal of Biological Chemistry 1999, vol. 274, No. 53, pp. 37533-37537.

(Continued)

Primary Examiner — Bin Shen
(74) Attorney, Agent, or Firm — Roche Diagnostics Operations, Inc.

(57) ABSTRACT

The present invention provides for stable nicotinamide adenine dinucleotide (NAD/NADH) and nicotinamide adenine dinucleotide phosphate (NADP/NADPH) derivatives of formula (I), enzyme complexes of these derivatives and their use in biochemical detection methods and reagent kits.

25 Claims, 12 Drawing Sheets

(56) References Cited

OTHER PUBLICATIONS

Hentall, et al., "Enhanced acid stability of a reduced nicotinamide adenine dinucleotide (NADH) analogue", Chem. Commun., 2001, pp. 2098-2099.

Lin, et al., "On the role of surface tension in the stabilization of globular proteins", Protein Science, 1996, 5, pp. 372-381.

Perl, et al., "Two exposed amino acid residues confer thermostability on a cold shock protein", Nature Structural Biology, May 2000, vol. 7, No. 5, pp. 380-383.

Sanbongi, et al., "Thermostability of Cytochrome c-552 from the Thermophilic Hydrogen-Oxidizing Bacterium Hydrogenobacter thermophilus", Biochemistry 1989. 28, pp. 9574-9578.

Schebor, et al., "Glassy State and Thermal Inactivation of Invertase and Lactase in Dried Amorphous Matrices", Biotechnol. Prog. 997, 13, pp. 857-863.

Zavodszky, et al., "Disulfide bond effects on protein stability: Designed variants of Cucurbita maxima trypsin inhibitor-V", Protein Science, 2001, 10, pp. 149-160.

\* cited by examiner

STABLE NAD/NADH DERIVATIVES

PRIORITY CLAIM

The present application is based on and claims the priority benefit of PCT Application Net WO 2007/012494, filed Jul. 28, 2006, which claims the priority benefit of German Patent Application No. DE 10 2005 035 461.0, filed Jul. 28, 2005, each of which are hereby incorporated by reference in their entireties.

TECHNICAL FIELD OF THE INVENTION

The invention concerns stable nicotinamide adenine dinucleotide (NAD/NADH) and nicotinamide adenine dinucleotide phosphate (NADP/NADPH) derivatives, enzyme complexes of these derivatives, and their use in biochemical detection methods and reagent kits.

BACKGROUND OF THE INVENTION

Measuring systems for biochemical analytics are important components of clinically relevant analytical methods. This primarily concerns the measurement of analytes e.g. metabolites or substrates which are determined directly or indirectly with the aid of an enzyme. The analytes are converted with the aid of an enzyme-coenzyme complex and subsequently quantified. In this process the analyte to be determined is brought into contact with a suitable enzyme and a coenzyme where the enzyme is usually used in catalytic amounts. The coenzyme is changed e.g. oxidized or reduced by the enzymatic reaction. This process can be detected electrochemically or photometrically either directly or by means of a mediator. A calibration provides a direct correlation between the measured value and the concentration of the analyte to be determined.

Coenzymes are organic molecules which are covalently or non-covalently bound to an enzyme and are changed by the conversion of the analyte. Prominent examples of coenzymes are nicotinamide adenine dinucleotide (NAD) and nicotinamide adenine dinucleotide phosphate (NADP) from which NADH and NADPH respectively are formed by reduction.

Measuring systems known from the prior art are characterized by a limited shelf-life and by special requirements for the environment such as cooling or dry storage in order to achieve this storage life. Hence erroneous results caused by incorrect, unnoticed, faulty storage can therefore occur for certain forms of application e.g. in the case of tests which are carried out by the end-users themselves such as glucose self-monitoring. In particular the exhaustion of desiccants due to opening of the primary packaging for excessive periods can result in measuring errors which in some systems can be hardly recognized by the consumer.

A known measure that can be used to increase the stability of biochemical measuring systems is the use of stable enzymes e.g. the use of enzymes from thermophilic organisms. It is also possible to stabilize enzymes by chemical modification e.g. cross-linking or by mutagenesis. Furthermore, enzyme stabilizers such as trehalose, polyvinylpyrrolidone and serum albumin can also be added or the enzymes can be enclosed in polymer networks e.g. by photopolymerization.

It has also been attempted to improve the storage life of biochemical measuring systems by using stable mediators. Thus the specificity of tests is increased and interferences during the reaction are eliminated by using mediators having the lowest possible redox potential. However, the redox potentials of the enzyme/coenzyme complexes constitute a lower limit for the redox potential. If one falls below this limit, this reaction with, the mediators is slowed down or even prevented.

Alternatively it is also possible to use biochemical measuring systems without mediators in which for example coenzymes such as the coenzyme NADH are directly detected. However, a disadvantage of such measuring systems is that coenzyme a such as NAD and NADP are unstable.

NAD and NADP are base-labile molecules the degradation paths of which are described in the literature (N. J. Oppenheimer in The Pyridine Nucleotide Coenzymes Academic Press, New York, London 1982, J. Everese, B. Anderson, K. Yon, Editors, chapter 3, pages 56-65). Essentially ADP-ribose is formed during the degradation of NAD or NADP by cleavage of the glycosyl bonds between the ribose and the pyridine unit. The reduced forms NADH and NADPH are, however, acid labile; e.g. epimerization is a known degradation path. In both cases the instability of NAD/NADP and NADH/NADPH is due to the lability of the glycosyl bond between the ribose and the pyridine unit. But even under conditions that are not drastic such as in aqueous solution, the coenzymes NAD and NADP are already hydrolysed solely by the ambient humidity. This instability can result in inaccuracies when measuring analytes.

A number of NAD/NADP derivatives; are described for example, in B. M. Anderson in the Pyridine Nucleotide Coenzymes, Academic Press New York, London 1982, J. Everese, B. Anderson, K. You, Editors, Chapter 4. However, most of these derivatives are not accepted well by enzymes. The only derivative which has therefore been previously used for diagnostic tests is 3-acetylpyridine adenine dinucleotide (acetyl NAD) which was first described in 1956 (N. O. Kaplan, J. Biol. Chem. (1956) 221, 823). This coenzyme is also not accepted well by enzymes and exhibits a change in the redox potential.

The use of other NAD derivatives with a modified pyridine group is described in WO 01/94370. However, modifications of the nicotinamide group usually have a direct effect on the catalytic reaction. In most cases this effect is negative.

In another stabilization concept the ribose unit was modified in order to influence the stability of the glycosyl bond. This process does not directly interfere with the catalytic reaction of the nicotinamide group. However, there may be an indirect effect as soon as the enzyme binds strongly and specifically to the ribose unit. In this connection Kaufmann et. al. disclose a number of thioribose-NAD derivatives in WO 98/33936 and U.S. Pat. No. 5,801,006 and/or WO 01/49247. However, a correlation between the modification of the nicotinamide ribose unit and the activity of the derivatives in enzymatic reactions has previously not been demonstrated.

CarbaNAD, a derivative without a glycosyl bond was described for the first time in 1988 (J. T. Slama, Biochemistry 1989, 27, 183 and Biochemistry 1989, 28, 7866). In this derivative the ribose is substituted by a carbacyclic sugar unit. Although carbaNAD was described as a substrate for dehydrogenases, its activity has not yet been proven in clinical biochemical detection methods.

A similar approach was described later by G. M. Blackburn, Chem. Comm., 1996, 2765 in order to synthesize carbaNAD with a methylene bisphosphonate linkage instead of the natural pyrophosphate. The methylene bisphosphonate shows higher stability towards phosphatases and was used as an inhibitor for ADP ribosyl cyclase. The aim was not to make it more resistant to hydrolysis (J. T. Slama, G. M. Blackburn).

Hence the object of the present invention is to provide stable bioanalytical measuring systems for determining an analyte such as glucose which avoid the sensitivity to hydrolysis of NAD/NADP and at the same time are active as coenzymes in enzyme reactions.

BRIEF DESCRIPTION OF THE DRAWINGS

The invention is described in more detail below on the basis of illustrative embodiments. However, the invention is not limited to the illustrative embodiments given here. The illustrative embodiments are shown schematically in the figures. Identical reference numbers in the individual figures designate elements which are identical or whose functions are identical, or which correspond to one another in terms of their function.

DETAILED DESCRIPTION OF EMBODIMENTS OF THE PRESENT INVENTION

Figure 1:
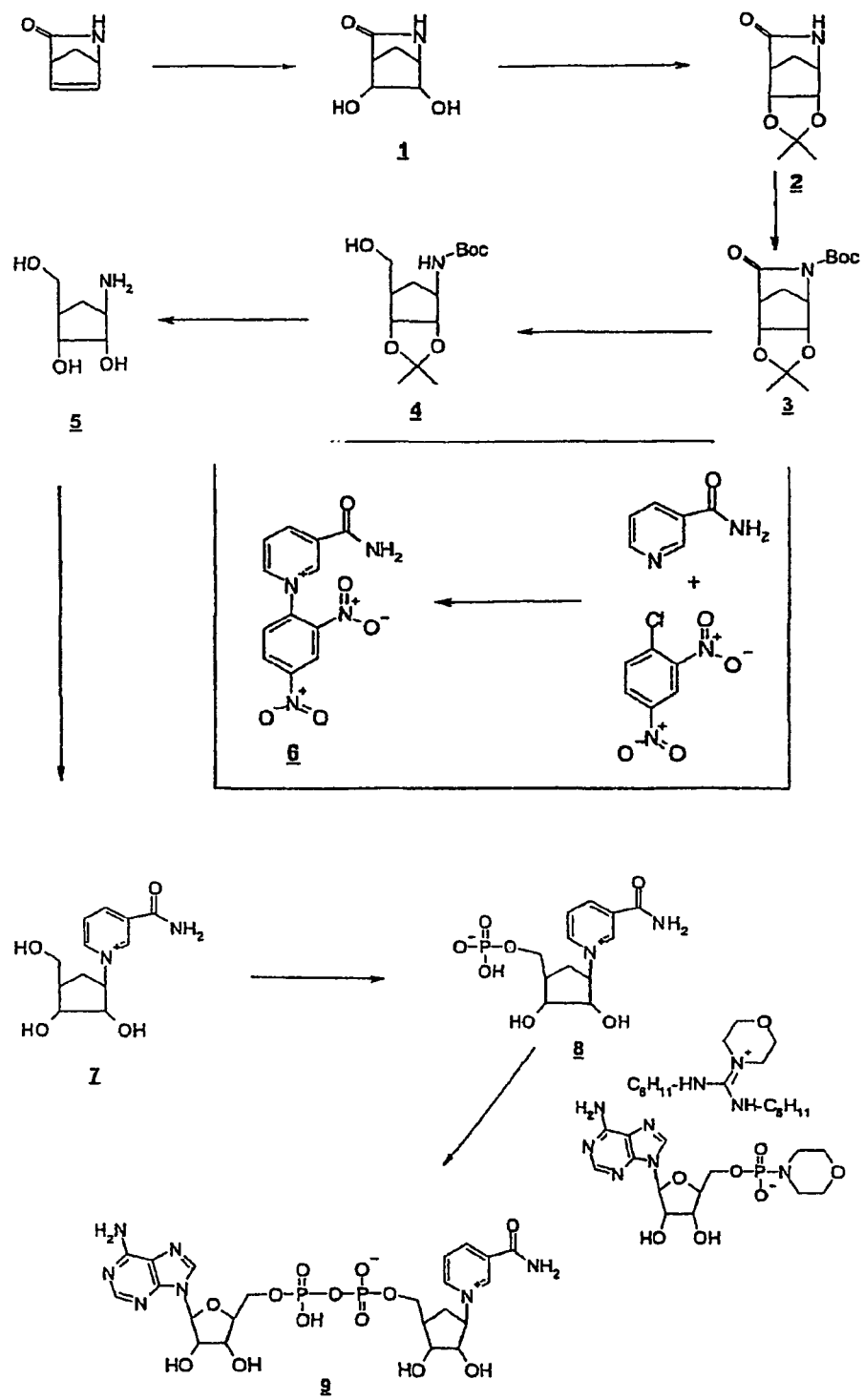
FIG. 1 illustrates a diagram of an embodiment of a process for synthesizing carbaNAD (cNAD).

The following description of embodiments of the present invention is merely exemplary in nature and is in no way intended to limit the present invention or its application or uses.

Embodiments of the present invention pertain to a test element configured for determining an analyte, comprising (i) a coenzyme-dependent enzyme or a substrate for such an enzyme and a compound of the following general formula (I) as the coenzyme:

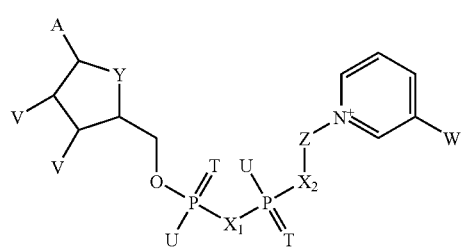

(I)

in which
A=adenine or an analogue thereof,
T=in each case independently denotes O, S,
U=in each case independently denotes OH, SH, $BH_3^-$, $BCNH_2^-$,
V=in each case independently denotes OH or a phosphate group,
W=COOR, $CON(R)_2$, COR, $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, $NCH_3$,
Y=NH, S, O, $CH_2$,
Z=a residue comprising a cyclic group with 5 C atoms which optionally contains a heteroatom selected from O, S and N and optionally one or more substituents, and a residue $CR4_2$ wherein $CR4_2$ is bound to the cyclic group and to X2 where R4=in each case independently denotes H, F, Cl, $CH_3$, provided that Z and the pyridine residue are not linked by a glycosidic bond, or a salt or optionally a reduced form thereof.

In one embodiment, W=$CONH_2$ or $COCH_3$.

Exemplary substituents on Z are selected from the group consisting of OH, F, Cl, and $C_1$-$C_2$ alkyl which are optionally fluorinated or chlorinated or/and OH-substituted, O—$C_1$-$C_2$-alkyl.

In another embodiment, a first residue V is OH and a second residue V is a phosphate group. Optionally the one OH group and the one phosphate group can form a ring together with the carbon atoms to which they are bound.

In yet another embodiment, the test element is provided that is configured to determine glucose and comprises a glucose dehydrogenase and a compound of the general formula (I) as mentioned above or a salt thereof.

Surprisingly the compounds according to the invention are generally stable towards hydrolysis and are good substrates in enzymatic detection methods and can be used for biochemical diagnostics. This finding is in contrast to that of most of the previously known NAD/NADP derivatives since these derivatives are usually stable for only very short periods in enzymatic detection methods.

The advantages of the compounds according to the invention compared to the prior art include:
high stability,
high enzymatic activity,
simple and economic synthesis,
they can be used in all previously known biochemical detection methods.

The disadvantages of the previously known biochemical, detection methods can be largely avoided by the provision of stable NAD/NADP derivatives using the present invention such as in combination with a stabilizing formulation such as for example by enclosing enzymes in polymer networks. Moreover, it is not necessary to use stabilizing additives. This is particularly advantageous since the lower the number of reactive substances involved, the greater is the chance of obtaining a stable formulation for the analyte determination.

Embodiments of the present invention provide test elements comprising a number of stable NAD/NADP derivatives which have aft adequate enzymatic activity for use as a coenzyme on the test element.

Stable NAD/NADP derivatives can be produced in generally known processes of synthesis. For this the amino group of a cyclic amino alcohol is converted into a pyridinium derivative by Zincke chemistry. The primary OH group is subsequently phosphorylated and coupled to an activated AMP derivative to form an NAD derivative. Alternatively the primary OH group can also be firstly phosphorylated and then the amino group can be converted into a pyridine by means of the Zincke reaction.

Another synthetic route is to activate the primary alcohol to form a tosylate or iodide and subsequently alkylate ADP.

Embodiments of the test element according to the invention comprise for example compounds having the following general formula (I'):

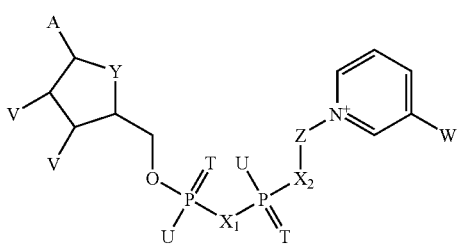

(I')

in which
A=adenine or an analogue thereof,
T=in each case independently denotes O, S,
U=in each case independently denotes OH, SH, $BH_3^-$; $BCNH_2^-$;
V=in each case independently denotes OH or a phosphate group,
W=COOR, $CON(R)_2$, COR, $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, $NCH_3$,
Y=NH, S, O, $CH_2$,
Z=a saturated or unsaturated carbocyclic or heterocyclic five-membered ring, in particular a compound, of the general formula (II)

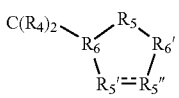

(II)

in which a single or double bond can be present between R5' and R5",
R4=in each case independently denotes H, F, Cl, $CH_3$,
R5=$CR4_2$,
if a single bond is present between R5' and R5", then
R5'=O, S, NH, $NC_1$-$C_2$-alkyl, $CR4_2$, CHOH, $CHOCH_3$,
R5"=$CR4_2$, CHOH, $CHOCH_3$,
if a double bond is present between R5' and R5", then
R5'=R5"=CR4,
R6, R6'=in each case independently denote CH, $CCH_3$
or a salt or optionally a reduced form thereof.

Compounds of the following general formula (I") are another subject matter of the invention:

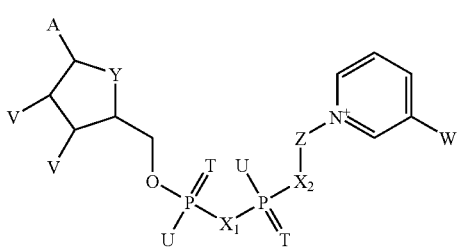

(I")

in which
A=adenine or an analogue thereof,
T=in each case independently denotes O, S,
U=in each case independently denotes OH, SH, $BH_3^-$, $BCNH_2^-$,
V=in each case independently denotes OH or a phosphate group,
W=COOR, $CON(R)_2$, COR, $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, $NCH_3$,
Y=NH, S, O, $CH_2$,
Z=a saturated or unsaturated carbocyclic or heterocyclic five-membered ring, in particular compounds of the general formula (II)

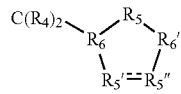

(II)

in which a single or double bond can be present between R5' and R5",
R4=in each case independently denotes H, F, Cl, $CH_3$,
R5=$CR4_2$,
if a single bond is present between R5' and R5", then
R5'=O, S, NH, $NC_1$-$C_2$-alkyl, $CR4_2$, CHOH, $CHOCH_3$,
R5"=$CR4_2$, CHOH, $CHOCH_3$,
if a double bond is present between R5' and R5", then
R5'=R5"=CR4,
R6, R6'=in each case independently denote CH, $CCH_3$
provided, that if R5=$CH_2$, T=O, U=in each case denotes OH, V=OH, W=$CONH_2$, X=O and Y=O then R5' and R5" are not simultaneously CHOH,
or a salt or optionally a reduced form thereof.

In a preferred embodiment the compounds according to the invention contain adenine analogues such as $C_8$-substituted and $N_6$-substituted adenine, deaza variants such as 7-deaza aza variants such as 8-aza or combinations such as 7-deaza or 8-aza or carbocyclic analogues such as formycin where the 7-deaza variants can be substituted in the 7 position with halogen, $C_1$-$C_6$-alkinyl $C_1$-$C_6$-alkenyl or $C_1$-$C_6$-alkyl.

In a further embodiment the compounds contain adenosine analogues which contain for example 2-methoxydeoxyribose, 2'-fluorodeoxy-ribose, hexitol, altritol or polycyclic analogues such as bicyclic, LNA and tricyclic sugars instead of ribose.

In particular (di)phosphate oxygens can also be isoelectronically substituted such as for example $O^-$ by $S^-$ and/or by $BH_3^-$, O by NH, $NCH_3$ and/or by $CH_2$ and =O by =S.

In one embodiment at least one residue U of the compound according to the invention is different from OH and in other embodiments at least one residue U=$BH_3^-$.

Yet other embodiments are the derivatives borano carba-NAD, c-pentyl NAD, pyrrolyl NAD, furanyl NAD, carba-NADcyclophosphate, carbaNADP, pyrrolidinyl NAD as well as test elements which contain them:

7
8
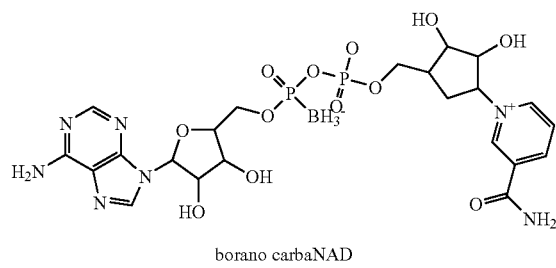
borano carbaNAD
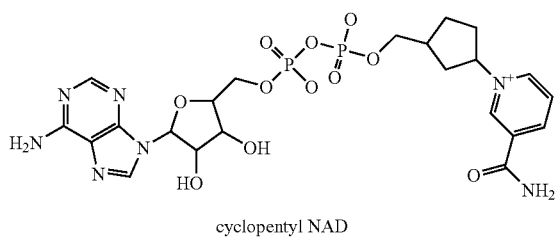
cyclopentyl NAD
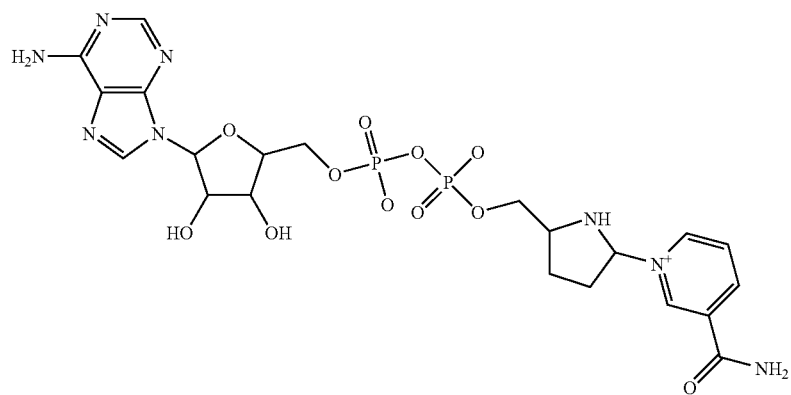
pyrrolyl NAD
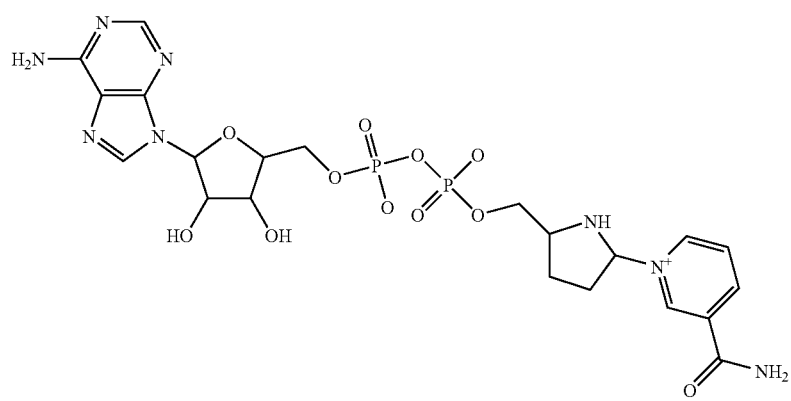
furanyl NAD
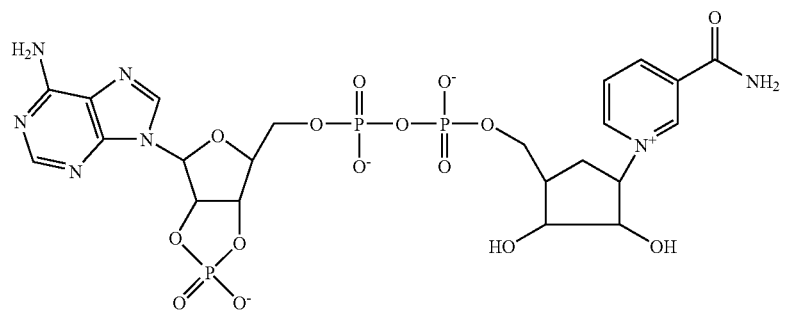
carbaNAD cyclophosphate -continued

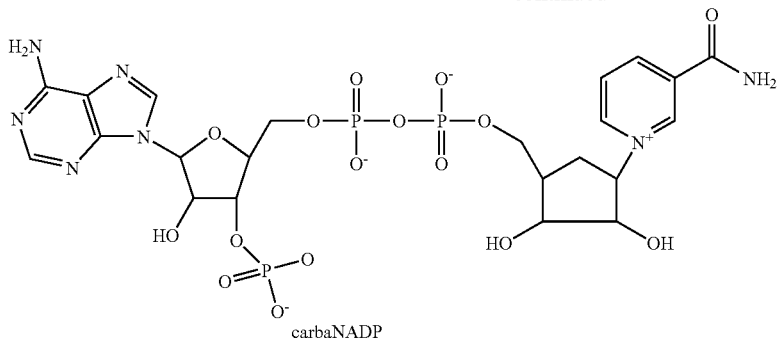
carbaNADP

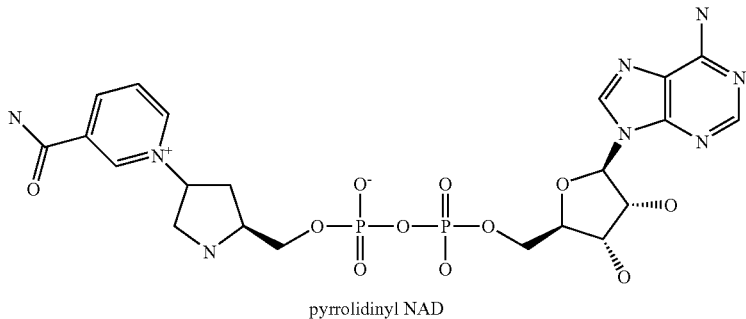
pyrrolidinyl NAD

Biochemical detections of analytes, for example parameters in body fluids such as blood, serum, plasma or urine or in samples of waste water of foods are of major importance in diagnostics. In these tests the analyte to be determined is brought into contact with a suitable enzyme and a coenzyme provided on a test element.

Hence, another subject matter of the present invention is an enzyme-coenzyme complex comprising a compound according to the invention in combination with a suitable enzyme.

Any biological or chemical substances that can be detected by a redox reaction can be determined as analytes e.g. substances which are substrates of a coenzyme-dependent enzyme or the coenzyme-dependent enzymes themselves. Examples of analytes are glucose, lactic acid, malic acid, glycerol, alcohol, cholesterol, triglycerides, ascorbic acid, cysteine, glutathione, peptides, urea, ammonium, salicylate, pyruvate, 5'-nucleotidase, creatine kinase (CK), lactate dehydrogenase (LDH), carbon dioxide etc.

For the detection of enzyme substrates, embodiments of a test element may contain an enzyme that is suitable for detecting the substrate, in addition to the coenzyme. Suitable enzymes are for example dehydrogenases selected from glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1.1.6), alcohol dehydrogenase (E.C.1.1.1.1), alpha-hydroxybutyrate dehydrogenase, sorbitol dehydrogenase, and amino acid dehydrogenase e.g. L-amino acid dehydrogenase (E.C.1.4.1.5). Further suitable enzymes are oxidases such as glucose oxidase (E.C.1.1.3.4) or cholesterol oxidase (E.C.1.1.3.6) or aminotransferases such as aspartate or alanine aminotransferase, 5'-nucleotidase or creatine kinase.

For the detection of enzymes, embodiments of a test element may contain an enzyme substrate suitable for detecting the enzyme, in addition to the coenzyme.

Another aspect of the present invention is the use of a compound according to the invention or of an enzyme-coenzyme complex according to the invention to detect an analyte in a sample by an enzymatic reaction. In this connection the detection of glucose with the aid of glucose dehydrogenase (GlucDH) is an exemplary use.

The change in the coenzyme i.e. in the compound according to the invention by reaction with the analyte (if the analyte is an enzyme substrate) or by an analyte-catalysed reaction (if the analyte is an enzyme) can in principle be detected in any desired manner. Basically all methods for detecting enzymatic reactions that are known from the prior art can be used. For example, the change in the coenzyme can be detected by optical methods. Optical detection methods for example include the measurement of absorption, fluorescence, circular dichroism (CD), optical rotary dispersion (ORD), refractometry etc. Fluorescence measurement in particular is highly sensitive and enables the detection even of low concentrations of the analyte in miniaturized systems.

A liquid test can be used to detect an analyte in which the reagent is for example present in the form of a solution or suspension in an aqueous or non-aqueous liquid or it is present as a powder or lyophilisate. It is, however, also possible to use a dry test, in which case the reagent is applied to a carrier, such as a test strip. The carrier can for example be a test strip comprising an absorbent or/and swellable material that is wetted by the sample liquid to be examined.

A gel matrix in which an enzyme-coenzyme complex is incorporated can, however, also be used as a detection reagent (cf. DE 102 218 45 A1).

In this case the enzyme can either be polymerized into the matrix together with the compound, according to the invention or, after the polymerization, the matrix can be contacted with a solution of the coenzyme in the presence of the enzyme to form the corresponding enzyme-coenzyme complex.

Another aspect of the present invention concerns a reagent kit and its use to detect analytes. The reagent kit can contain a compound according to the invention, a suitable enzyme and a suitable reaction buffer. Suitable enzymes have already been described. The reagent kit according to the invention can be used in a wide variety of ways and can be used to determined analytes such as glucose, lactic acid, malic acid, glycerol, alcohol, cholesterol triglycerides, ascorbic acid, cysteine, glutathione, peptides, urea, ammonium, salicylate, pyruvate, 5'-nucleotidase, CK, LDH and carbon dioxide etc. In one embodiment, a reagent kit is provided which contains a compound according to the invention and glucose dehydrogenase (E.C.1.1.1.47) to detect glucose in blood.

The reagent kit according to the invention can be used to detect an analyte in a dry or liquid test.

Another aspect of the present invention concerns a test strip for the fluorometric or photometric detection of an analyte. Such a test strip contains a compound as stated above as a coenzyme and a suitable enzyme or an enzyme substrate immobilized on an absorbent or/and swellable material. Suitable materials can for example be selected from cellulose, plastics etc.

Another aspect of the present invention comprises a method for detecting an analyte comprising the steps:
(a) contacting a sample with a test element or reagent kit according to the invention comprising a coenzyme; and
(b) detecting the analyte e.g. on the basis of a change in the coenzyme.

One aspect of the invention is that the fluorescence emission of the coenzymes exhibits a bathochromic shift and hence there is low interference with the fluorescence emission of other materials of the test element or/and of the sample.

All embodiments of the aspects of the present invention that are described and/or shown are also intended to apply to other aspects of the invention such as, e.g., embodiments of the compounds according to the invention.

EXAMPLES

Experimental Preparation Of Stable NAD/NADH Derivatives

Figure 5:
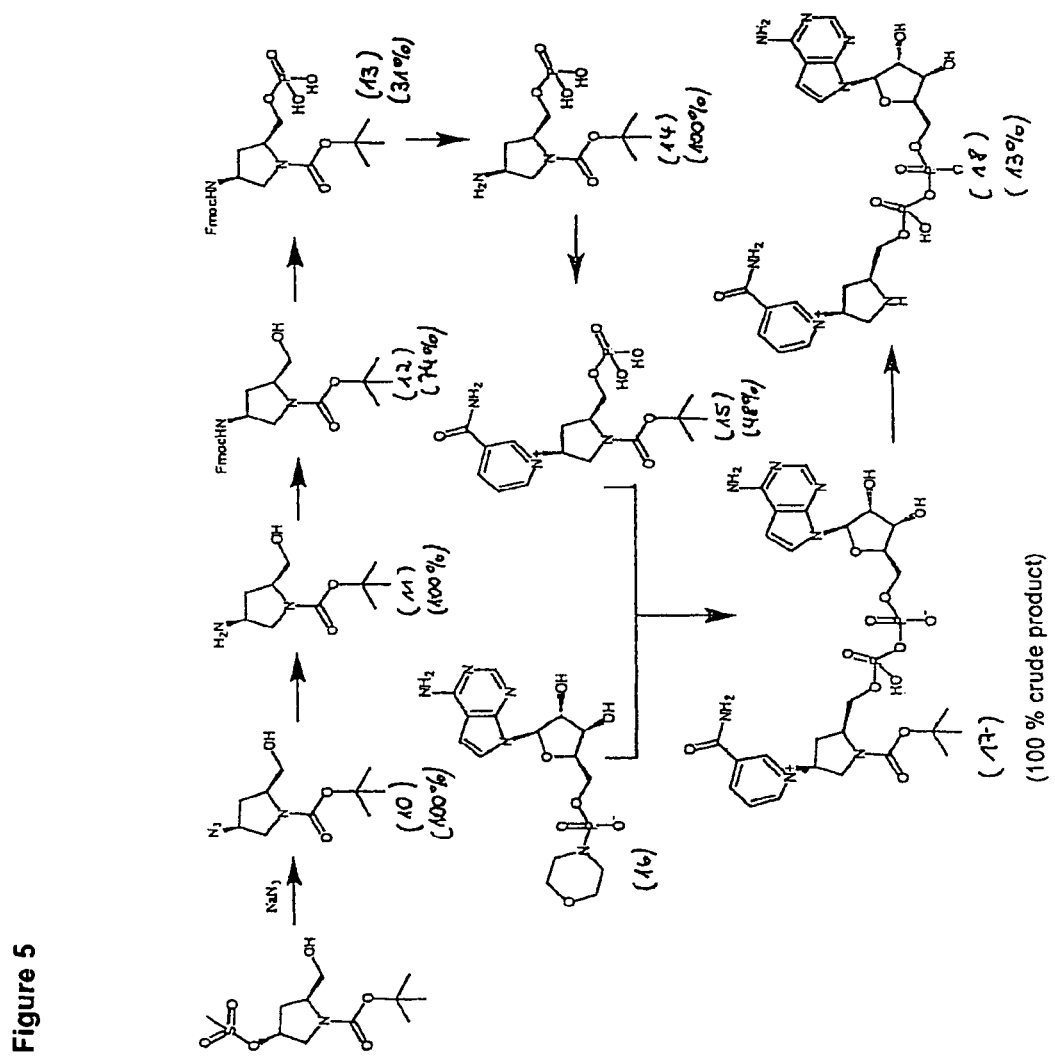
FIG. 5 illustrates a diagram of an embodiment of a process for synthesizing pyrrolidinyl NAD (pNAD), including compound numbers and yields of the respective reaction steps being stated next to the structural formulae.

The preparation of stable NAD/NADH derivatives is shown on the basis of carbaNAD (compound 9, FIG. 1) and pyrrolidine NAD (compound 18, FIG. 5) as examples. Additional derivatives can be prepared using appropriate processes of synthesis. The corresponding amino alcohols used as starting reagents are known in the literature; 2-amino-1,4-anhydro-2,3-dideoxy-L-threo-pentitol: Huryn, Donna M.; Sluboski, Barbara C.; Tam, Steve Y.; Todaro, Louis J.; Weigele, Manfred Tetrahedron Letters (1989), 30(46), 6259-62,
3-amino-, (1R,3S)-cyclopentanemethanol, Beres, J.; Sagi, G.; Tomoskozi, I.; Gruber, L.; Gulacsi, E.; Otvos, L.; Tetrahedron Letters (1988), 29(22), 2681-4.

A) Preparation of carbaNAD

I. 1R-(−)-exo-cis-5,6-dihydroxy-2-azabicyclo[2.2.1]heptan-3-one (1)

A solution of 16.4 g (147 mmol) 1R-(−)-2-azabicyclo[2.2.1]hept-5-en-3-one in 400 ml acetone is added to a solution of 22.5 g (167 mmol) N-methyl-morpholine-N-oxide in 80 ml deionised water in a 1 L round-bottomed flask. 15 ml (1.2 mmol) of a 2.5% solution of osium tetraoxide in tert-butanol is added within 15 min while cooling on ice. The mixture is subsequently stirred overnight at room temperature.

The solvent is removed by distillation in a rotary evaporator. It is stirred with 100 ml and again distilled off in a rotary evaporator. Afterwards it is dissolved in 600 ml deionised water and 35 g activated carbon is added. The mixture is stirred vigorously for 1 h and then filtered over a Seitz K 250 deep-bed filter. Water is removed from the filtrate by distillation in a rotary evaporator. The product is used without further purification.

TLC (Merck silica gel 60 F-254); ethyl acetate/methanol/glacial acetic acid 7:2:1 $R_f$ 0.75 (starting material), 0.53 (1). Staining with TDM/development in a chlorine chamber.

* TDM reagent: Solution 1: 10 g N,N,N',N'-tetramethyl-4,4'-diamino-diphenyl methane in 40 ml glacial acetic acid and 200 ml deionised water. Solution 2: 20 g potassium chloride in 400 ml deionised water. Solution 3; Dissolve 0.3 g ninhydrin in 10 ml glacial acetic acid and add 90 ml deionised water. Finished reagent: A mixture of solution 1 and 2 and addition of 6 ml of solution 3.

II 1R-(−)-exo-cis-5,6-dimethylmethylenedioxy-2-azabicyclo[2.2.1]heptan-3-one (2)

The crude product 1 is boiled under reflux for 1 h in 200 ml absolute ethanol. After adding 400 ml (3.26 mol) dimethoxypropane and 250 mg (2.2 mmol) pyridine hydrochloride, the mixture is boiled under reflux for a further 15 min. After adding 10 ml saturated sodium hydrogen carbonate solution, the solution is evaporated to dryness under a vacuum in a rotary evaporator. 500 ml Chloroform, 150 ml saturated sodium chloride solution and 75 ml saturated sodium hydrogen carbonate solution are added to the residue and it is transferred into a separating funnel. After extraction by shaking it is allowed to stand overnight during which phase separation takes place.

The organic phase is separated and the aqueous phase is extracted for a further two times with 200 ml chloroform in each case. The combined organic phases are dried over magnesium sulfate. After removing the desiccant by filtration, the solvent is removed by distillation under reduced pressure on a rotary evaporator. The crude product (24.9 g=92%) is used without further purification.

TLC (Merck silica gel 60 F-254); ethyl acetate/methanol/glacial acetic acid 7:2:1 $R_f$ 0.84, Staining with TDM/development in a chlorine chamber).

III. 1R-(−)-4-N-tert-butyloxycarbonyl-exo-cis-5,6-dimethylmethylene-dioxy-2-2-azobicyclo[2.2.1]heptan-3-one (3)

41.5 g (190 mmol) di-tert-butyl dicarbonate and 0.83 g (6.8 mmol) 4-dimethyl-aminopyridine are added under argon to a solution of 24.9 g (135.7 mmol) crude product 2 in 450 ml absolute chloroform. The mixture is boiled under reflux while stirring until the gas evolution ceases. The mixture is filtered over a column that is filled with 40 g silica gel 60 and equilibrated with chloroform. It is washed with 100 ml chloroform. The solvent is removed from the filtrate by distillation under reduced pressure on a rotary evaporator. The crude product is dried for 60 min at 10 mbar and 40° C. It is used without further purification.

TLC (Merck silica gel 60 F-254): ethyl acetate/hexane 3:2 $R_f$ 0.85. Staining with TDM/development in a chlorine chamber).

IV. (−)-(1R,2R,3S,4R)-4-(N-tert-butyloxycarbonyl) amino-2,3-dimethylmethylenedioxy-1-(hydroxymethyl)cyclopentane (4)

The crude product 3 is dissolved at room temperature in 400 ml tetrahydrofuran while stirring and 80 ml deionised water is added. After cooling to 4° C. 5.3 g sodium borohydride is added all at once and stirred overnight during which the mixture is allowed to slowly heat up to room temperature. 100 ml ethanol is added and it is stirred for 6 h at room temperature. The solvents are removed by distillation under reduced pressure on a rotary evaporator, 300 ml saturated sodium chloride solution and 650 ml ethyl acetate are added and it is transferred to a separating funnel. The organic phase is separated and the aqueous phase is again washed with 350 ml ethyl acetate. The combined organic phases are dried over magnesium sulfate. After removing the desiccant by filtration, the solvent is removed by distillation under reduced pressure on a rotary evaporator. The crude product (42.2 g) is purified by means of column chromatography and silica gel 60 (column h=93 cm, d=10 cm) eluant THF/hexane 1:3, then THF/hexane 2:3), flow rate 3 L/h. 40 ml fractions are collected. The fractions are monitored by TLC (Merck silica gel 60 F-254: ethyl acetate/hexane 3:2 $R_f$ 0.45. Staining with TDM/development in a chlorine chamber). The solvent is removed from the combined product fractions by distillation in a vacuum on a rotary evaporator, yield: 24.9 g.

V. (-)-(1R,2R,3S,4R)-4-amino-2,3-dihydroxy-1-(hydroxymethyl)cyclo-pentane (5)

8 ml Deionised water and then 80 ml trifluoroacetic acid are added to 11.09 (38.6 mmol) 4. It is stirred vigorously for 6 h at room temperature during which a clear pale yellow solution forms. 200 ml deionised water is added and it is evaporated under a vacuum on a rotary evaporator. 200 ml deionised water is again added and it is again evaporated under a vacuum on a rotary evaporator. The crude product is dissolved in 100 ml deionised water in an ultrasonic bath and filtered. The filtrate is applied to a Dowex 1X8 (100-200 mesh, OH form) ion exchanger column (15×4.9 cm) and eluted with water during which the product elutes after about 150 ml in a volume of 300 ml (pH 10.4). The fractions are monitored by TLC (Merck silica gel 60 F-254: butanol/glacial acetic acid/water 5:2:3 $R_f$ 0.42, staining with TDM/development in a chlorine chamber). The solvent is removed from the combined product fractions by distillation in a vacuum on a rotary evaporator, yield: 5.2 g colourless oil.

VI. Zincke Salt of the Nicotinamide (6)

58.6 g Dinitrochlorobenzene is melted under nitrogen and then 29.32 g nicotinamide is added to the melt. It is heated for 2.5 h at 110° C., 500 ml of a 3:2 (v/v) ethanol/water mixture is added through a reflux cooler and it is boiled under reflux until a solution is formed. After stirring overnight at room temperature, 150 ml 50% ethanol/water and 100 ml water are added, it is transferred to a separating funnel and washed three times with 500 ml chloroform each time. 300 ml and 50 g active carbon are added to the separated aqueous phase which is stirred for 1 h at room temperature and then filtered over a Seitz K 700 deep-bed filter. The filtrate is concentrated in a vacuum to about 100 ml on a rotary evaporator during which the bath temperature must not exceed 20° C. It is diluted with 300 ml water and 70 g sodium tetrafluoroborate is added at room temperature while stirring. The precipitate is recrystallized from methanol/water. The crystallisate is removed by filtration, washed with a small amount of acetone and then with diethyl ether and dried for 24 h in a high vacuum at 40° C. (yield 21.1 g 23%). The fractions are monitored by TLC (Merck silica gel 60 F-254: butanol/glacial acetic acid/water 5:2:3 $R_f$ 0.56).

VII. (-)-(1R,2R,3S,4R)-4-(3-carboxamidopyridin-1-yl)-2,3-dihydroxy-1-(hydroxymethyl)cyclopentane (6)=carba Nicotinamide Mononucleoside=carbaNMN A solution of 4.5 g (31 mmol) cyclopentylamine 5 in 110 ml absolute methanol is added dropwise within 90 minutes to a solution of 15.3 g (40.7 mmol) of the Zincke salt 6 in 110 ml absolute methanol while stirring at room temperature. 1 ml diisopropylethylamine is added and it is then stirred for two days at room temperature. 500 ml water is added, transferred into a separating funnel and washed twice with 200 ml methylene chloride each time. The water is removed from the separated aqueous phase by distillation under a vacuum on a rotary evaporator. The residue is taken up in 100 ml water and purified by column chromatography on Sephadex C25 (Na+ form): column 70×7.5 cm elution of buffer A (deionised water) to buffer B 0.35 M NaCl in water, flow rate 200 ml/h. 15 ml fractions are collected and monitored by TLC (Merck silica gel 60 F-254: butanol/glacial acetic acid/water 5:2:3 $R_f$ 0.22).

The solvent is removed from the combined product fractions by distillation in a vacuum on a rotary evaporator. The salt-containing residue is boiled out with 500 ml hot ethanol. It is hot-filtered and allowed to stand for 12 h at room temperature. The precipitate is removed by filtration and the solvent is removed from the filtrate by distillation under a vacuum on a rotary evaporator. Yield 7 g.

VIII. (-)-(1R,2R,3S,4R)-4-(3-carboxamidopyridin-1-yl)-2,3-dihydroxy-1-phosphatoylmethyl)cyclopentane (6)=carba NMN-monophosphate A mixture of 20 ml phosphoroxy chloride and 50 ml trimethyl phosphate is added at 0° C. to a suspension of 7 g (27.7 mmol) carbaNMN in 80 ml anhydrous trimethyl phosphate. It is stirred for 2 h at 0° C. and then for 2 h at room temperature. 300 ml water is added while cooling on ice and the mixture is evaporated to 10 ml under a vacuum on a rotary evaporator. It is taken up in 100 ml water, filtered and purified by means of column chromatography on Sephadex C25 (NEt3H+ form): column 66×9 cm, elution of buffer A (deionised water) to buffer B) 0.60 M ammonium acetate, flow rate 200 ml/h. 15 ml fractions are collected and monitored by TLC (Merck silica gel 60 F-254 plates: isobutyric acid/ammonia/water 66:1:33, $R_f$ 0.25). The solvent is removed from the combined product fractions by distillation in a vacuum on a rotary evaporator. The residue is dissolved in 100 ml water and lyophilized. This procedure is repeated three times. Yield 4.0 g.

IX. carbaNAD (9)

A solution of 1.25 g (30 mmol) AMP morpholidate in 40 ml absolute DMF is added dropwise within 1 h at room temperature to a mixture of a solution of 3.31 g (10 mmol) carbaNMN monophosphate in 40 ml absolute DMF and 78 ml (39 mmol) 3.5% tetrazole in absolute acetonitrile. The mixture is stirred for 2 days at room temperature.

The pH is adjusted to 6.5 using an aqueous 10% $KHCO_3$ solution while cooling on dry ice/acetone. It is diluted with 500 ml water and carefully concentrated to dryness in a vacuum on a rotary evaporator. The residue is dissolved in 150 ml deionised water and purified by column chromatography on Sephadex QAE 25 (NEt3H+ form): column 65×4.5 cm, elution of buffer A (deionised water) to buffer B) 1 M triethylammonium carbonate, flow rate 200 ml/h: 15 ml fractions are collected and monitored by TLC (Merck silica gel 60 F-254 plates: isobutyric acid/ammonia/water 66:1:33, $R_f$ 0.47).

The solvent is removed by distillation from the combined product fractions by distillation in a vacuum on a rotary evaporator. The residue is dissolved in 100 ml water and lyophilized. This procedure is repeated three times. Yield 1.1 g.

Examination of the Stability of carbaNAD

A 10 mM solution of carbNAD and/or NAD is stressed at pH 8 in 0.1 M potassium phosphate buffer. The content is determined by means of HPLC chromatography after 0.25, 75 and 175 h.

Buffer A: 100 mM. $KHPO_4$+10 mM tetrabutylammonium hydrogen sulfate, pH 6.9 buffer B: buffer A+acetonitrile 1:1 flow rate 1.0 ml/min detection: 254 nm

RP18 column L 125 diameter 4.6 mm gradient: in 40 min to 35% buffer B, hold for 2 min and then change to 0% buffer A within 3 min.

Figure 2:
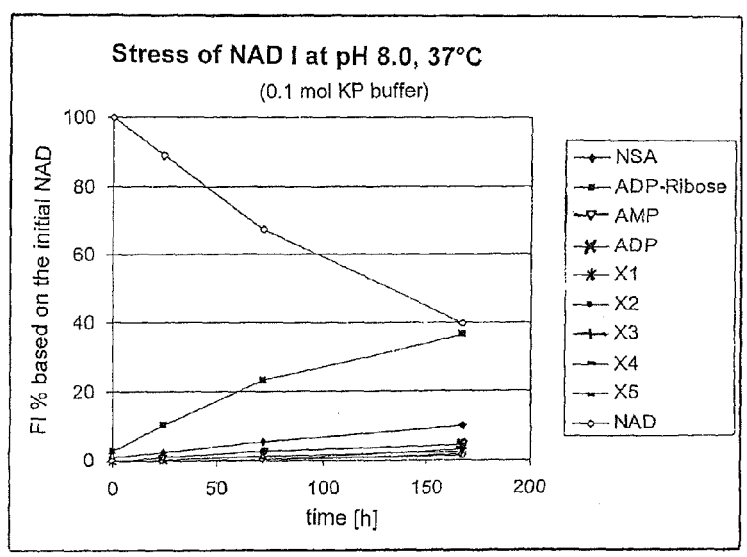
FIG. 2 shows a graph of the results of stressing NAD at a pH of 8.0 and 37° C.
Figure 3:
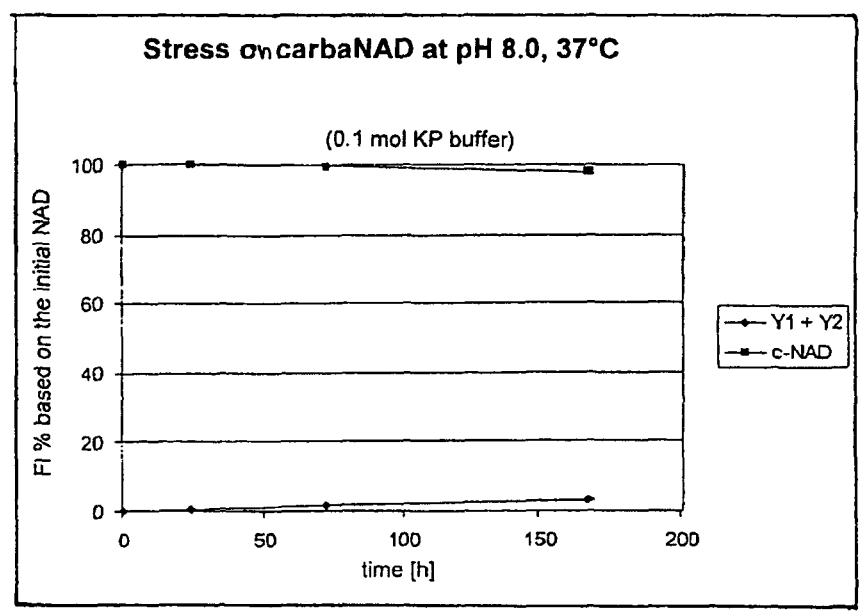
FIG. 3 shows a graph of the results of stressing carbaNAD at a pH of 8.0 and 37° C.
Figure 4:
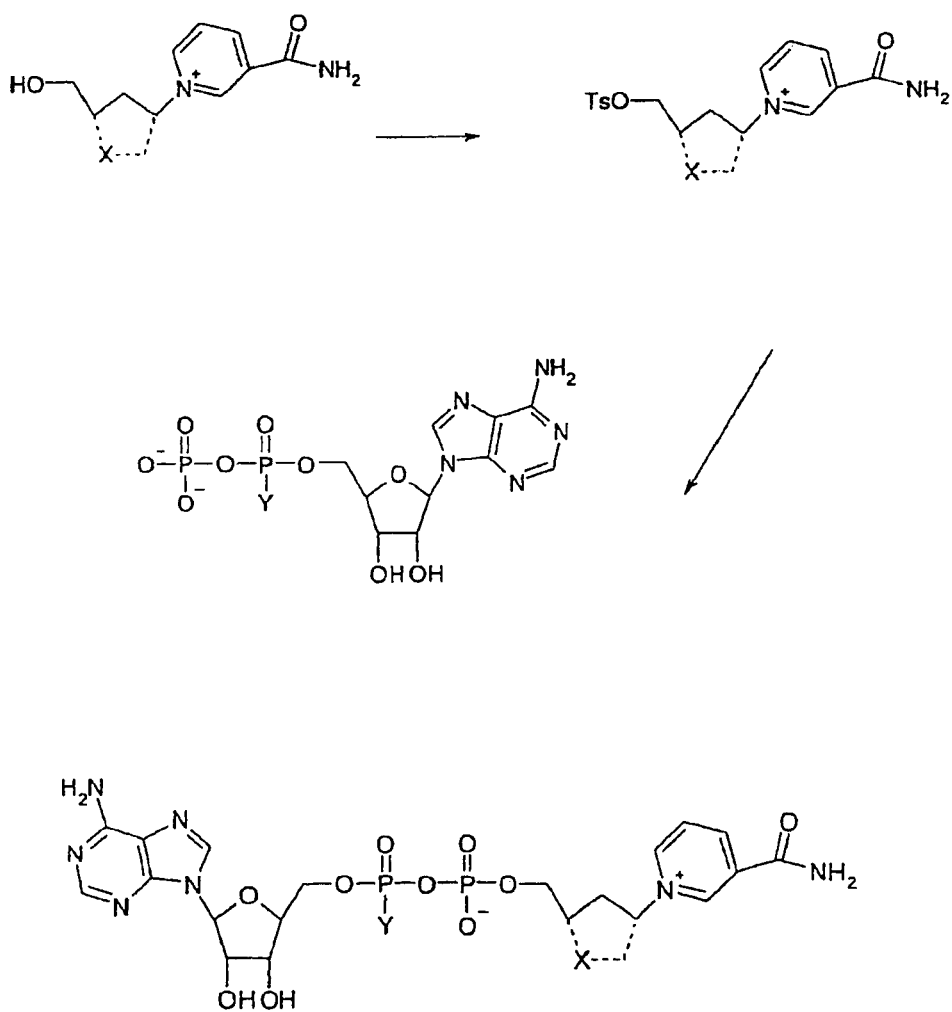
FIG. 4 illustrates a diagram of an embodiment of a process for synthesizing borano NAD by alkylating ADP, wherein in the case of Y=$BH_3$, only the beta phosphate of ADP is alkylated.

The HPLC area percentages after stressing for the various times are shown in FIGS. 2 and 3.

The occurrence of decomposition products (nicotinamide, ADP-ribose, AMP, ADP and the unknown decomposition products for NAD and the unknown decomposition products Y1 and Y2 for cNAD) show that cNAD is very stable compared to NAD.

B) Preparation of Pyrrolidinyl-NAD

I. Synthesis of pNAD 1st Stage (Compound 10)

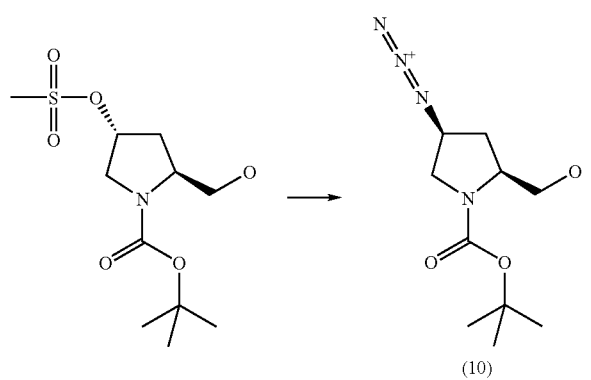 [SMILES: CC(C)(C)OC(=O)N1C[C@H](OS(C)(=O)=O)C[C@H]1CO ; CC(C)(C)OC(=O)N1C[C@@H](N=[N+]=N)C[C@H]1CO]

(10)

Trans-N-t-BOC—O-mesyl-4-hydroxyl-L-prolinol (35.4 g, 120 mmol) was dissolved in 500 ml DMF and sodium, azide (15.6 g, 240 mmol) dissolved in 75 ml water was added and heated for 5 h to 70° C., it was subsequently stirred farther overnight at room temperature, the mixture was poured into 1000 ml saturated sodium chloride solution and extracted with ethyl acetate. The ethyl acetate was dried with $Na_2SO_4$ and subsequently evaporated.

32.8 g (>100%) residue was formed (theoretical value: 29 g).

The crude product was directly processed further after TLC and MS monitoring. A thin layer chromatography on a KG 60 F-254 plate (mobile solvent: ethyl acetate/sprayed with ninhydrin) was carried out for the monitoring:

trans-N-t-BOC—O-mesyl-4-hydroxy-L-prolinol $R_f$: 0.49 product $R_f$: 0.78

MS ESI ES+ 242

The identity of the product was also confirmed by NMR analysis.

*trans-N-t-BOC—O-mesyl-4-hydroxyl-L-prolinol is commercially available from Sanochemia Pharmazeutika AG, Cat. No. P-719.

II. Synthesis of pNAD 2nd Stage (Compound 11)

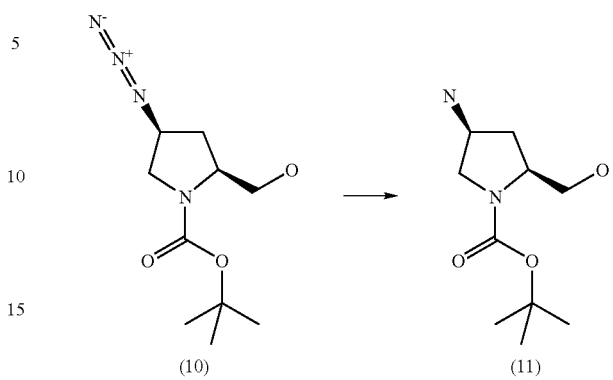

(10)                    (11)

Compound 10 (120 mol) was mixed in 500 ml methanol with 2.0 g Pd-carbon (10%) and hydrogenated for 12 h at 30 mbar. In this process the reaction flask was flushed several times with $H_2$, the catalyst was removed by suction filtration and it was concentrated.

A colourless oil was formed (the oil should be immediately processed further due to its high air-sensitivity).

MS ESI ES+ 217 present

TLC (isohexane/ethyl acetate 1/1/KG 254 F/ninhydrin): product remains at the start.

The identity of the product was also confirmed by NMR analysis.

III. Synthesis of pNAD 3rd Stage (Compound 12)

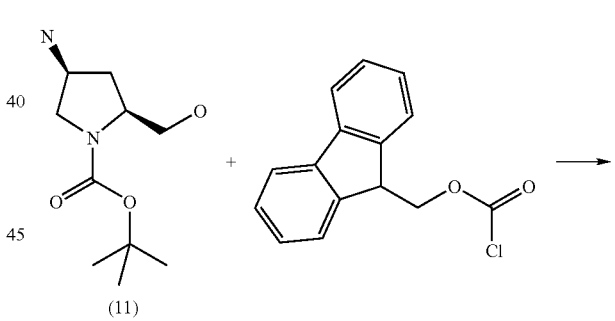

(11)

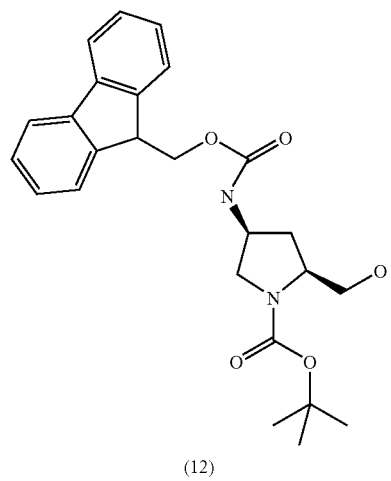

(12)

120 mmol of compound 11 (MW: 216.28) was mixed in 500 ml dioxane containing NaHCO$_3$, (11.0 g, 130 mmol) and Fmoc chloride (33.8 g, 130 mmol) and stirred overnight at room temperature. The resulting salts were removed by filtration, the solution was evaporated and the residue was purified over a silica gel column (isohexane and isohexane/EE 8/2-1/1).

The main fraction yielded 39.0 g=74.1% * (theoretical value=52.6 g).

TLC (KG 60 F254 mobile solvent isohexane/ethyl acetate 2:1): R$_f$ 0.13

MS ESI ES+439/+339

The identity of the product was also confirmed by NMR analysis.

* Yield refers to the educt of the 1st stage.

IV. Synthesis of pNAD 4th Stage (Compound 13)

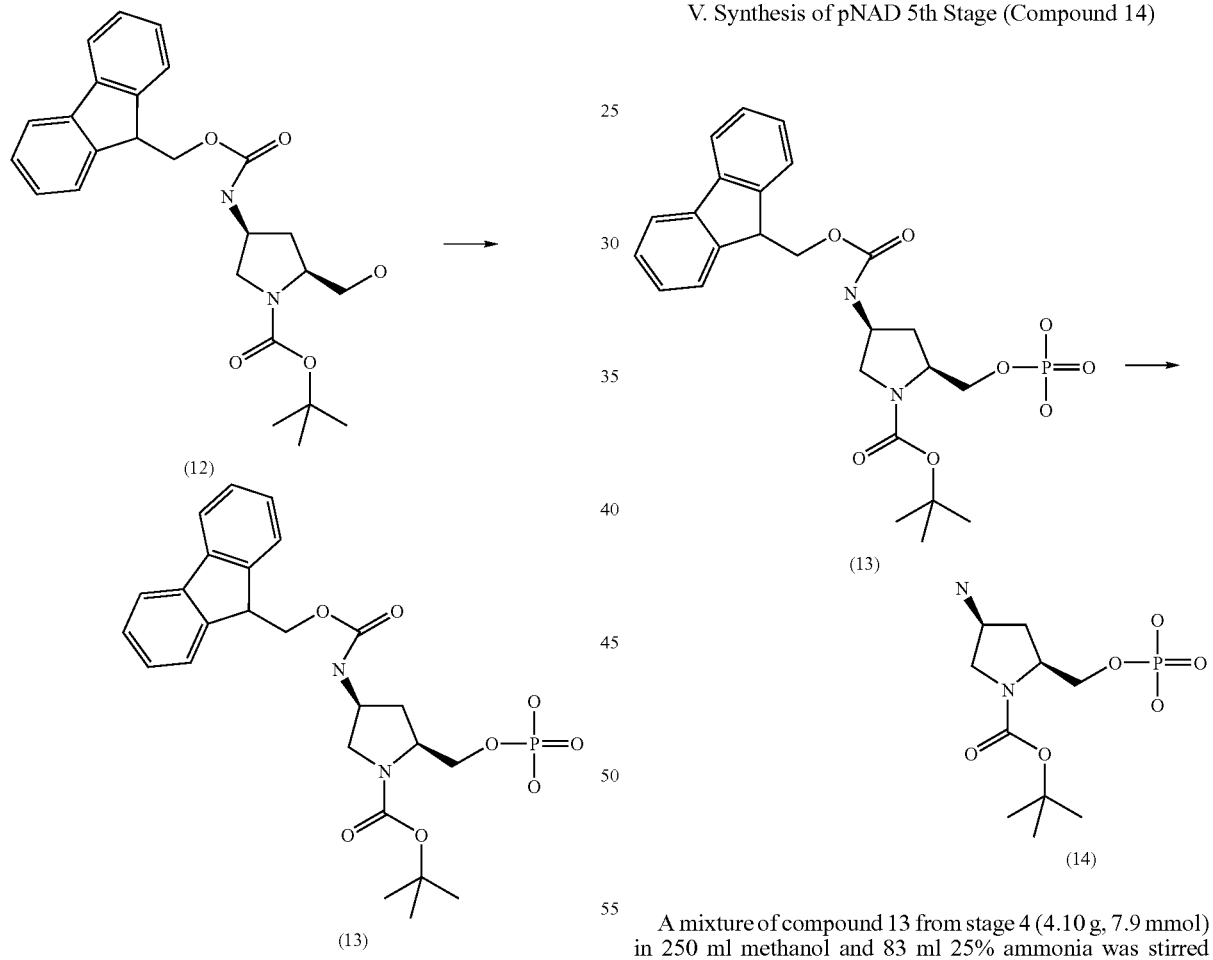

(12)

(13)

Compound 12 from stage 3 (7.08 g, 16.1 mmol) was dissolved in 80 ml trimethyl phosphate and subsequently cooled to 0° C. in an ice bath. POCl$_3$ mixed with trimethyl phosphate (13 ml freshly distilled POCl$_3$ in 13 ml trimethyl phosphate) was added to a dropping funnel and added in portions within 20 min under argon. The temperature increased in an exothermal reaction to up to 5° C. Subsequently 2.6 ml pyridine was added and it was stirred for a further 40 min at 0° C. and under argon.

The reaction solution was carefully added dropwise to 800 ml ice-cooled 1 M triethylammonium hydrogen carbonate solution (pH=8). After the addition was completed, it was stirred for a further 1 h. The slightly turbid solution was subsequently added (rapidly) dropwise to 1 L saturated NaCl solution. It was stirred further overnight to improve the crystallization. The precipitate was removed by filtration. The residue was desalted over a Diaion column. For this purpose 500 g Diaion was added to isopropanol/water 1/1 and allowed to swell-overnight. Diaion was filled into the column and rinsed with water. A slurry of the residue was formed in 100 ml water pH 3.5 (acetic acid) which was subsequently applied to a column and rinsed with water (pH 3.5) until it was free from sodium chloride. The substance was then eluted from the column with 25% isopropanol (pH 3.5). The solution was evaporated in a high vacuum at room temperature.

Residue=2.6 g=31.3%

TLC RP8 F254/MeOH/water 9/1

MS ESI ES−517.13

The identity of the product was also confirmed by NMR analysis.

V. Synthesis of pNAD 5th Stage (Compound 14)

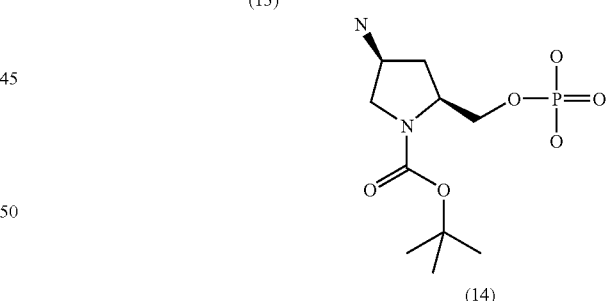

(14)

A mixture of compound 13 from stage 4 (4.10 g, 7.9 mmol) in 250 ml methanol and 83 ml 25% ammonia was stirred overnight at room temperature and evaporated in a vacuum at room temperature. The residue was taken up in 200 ml water and stirred out three times with 100 ml ethyl acetate. Insoluble components were removed by filtration; the clear water phase was separated and again evaporated at room temperature.

Residue=2.56 g=100%

MS ESI ES−295

In order to remove the NH$_3$ cations, the residue was dissolved 2× in Hünig's base and again evaporated each time in a high vacuum.

VI. Synthesis of pNAD 6th Stage (Compound 15)

VIIa. Synthesis of pNAD Stage 7a (Compound 16)

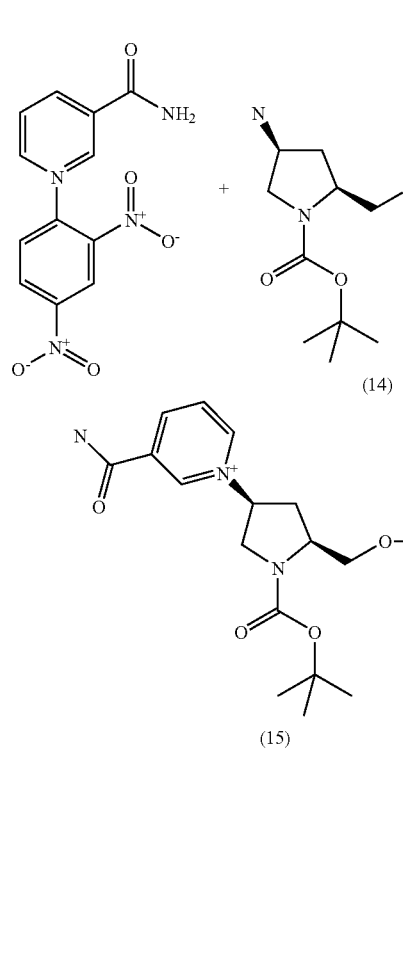

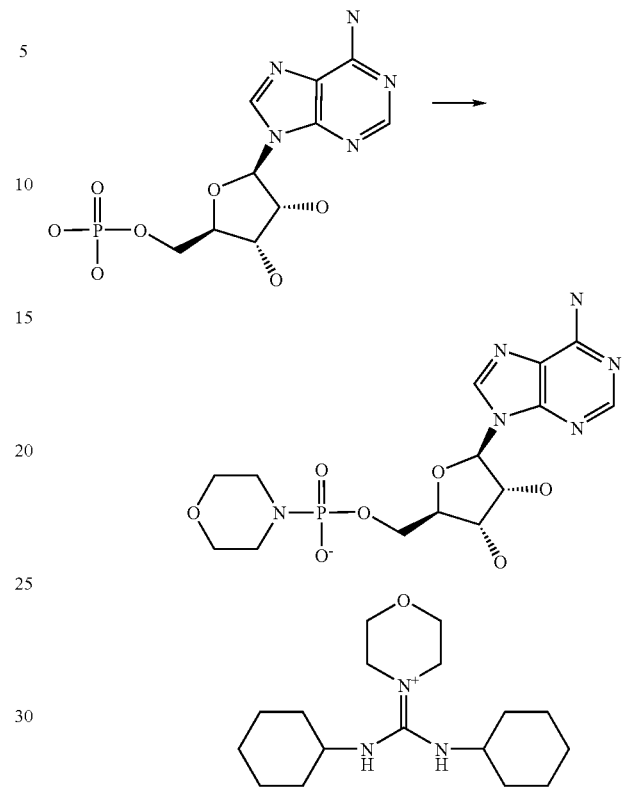

The Zincke salt (2.66 g, 8.99 mmol) was submitted partly dissolved in 50 ml methanol and compound 14 from stage 5 (2.56 g, 8.31 mmol) dissolved in 50 ml methanol was added dropwise while stirring. The mixture coloured red and slowly dissolved. It was stirred further overnight at room temperature and the precipitate was removed by filtration. The filtrate was evaporated in a vacuum, taken up in 100 ml water and extracted three times with ethyl acetate.

The ethyl acetate phase contains the by-product dinitroaniline, the water phase contains the product and the remaining Zincke salt. The water phase was evaporated in a vacuum at room temperature and 10 ml water was added to the residue that was obtained, which was stirred for 10 min on a magnetic stirrer and insoluble components were removed by filtration. The product remained dissolved. This solution was applied to a Diaion HP20 column (1000 ml) that had been rinsed with water and was rinsed two times with 1000 ml water. Subsequently it was rinsed with water/5% isopropanol and positive fractions (detected by TLC RP8 MeOH/W 9/1) were evaporated at room temperature. The residue was triturated with isopropanol and suction filtered with the aid of diethyl ether.

Residue=1.60 g=47.9%
TLC RP8 254 MeOH/W 9/1
MS ES−400.1/ES+402.0 also exhibits the double mass
The identity of the product was also confirmed by NMR analysis.

A mixture of AMP acid (adenosine monophosphate-free acid) (10 g, 27.5 mmol) in 60 ml methanol (dried with sodium) and 5.3 ml (60 mmol) morpholine (freshly distilled) was stirred until a clear solution was formed. Subsequently 17 g (82.5 mmol) N,N'-dicyclohexyl carbodiimide (DCC) was added and stirred overnight at room temperature while excluding moisture. The precipitate (DCH) that was formed was suction filtered and the filtrate was rotary evaporated at 30° C. Subsequently it was stirred out with 150 ml H₂O/150 ml diethyl ether and again filtered. After phase separation the aqueous phase was again extracted twice with 75 ml diethyl ether each time. The aqueous phase was subsequently rotary evaporated at room temperature. The residue was dissolved a further two times in pyridine and each time again rotary evaporated in a high vacuum.

VII. Synthesis of pNAD 7th Stage (Compound 17)

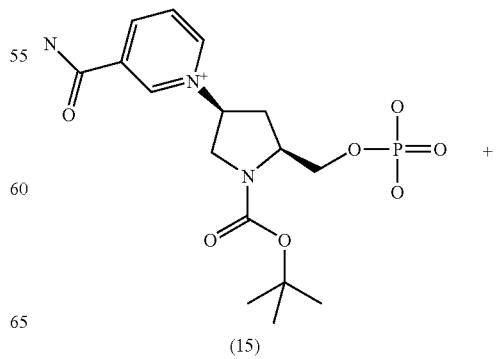

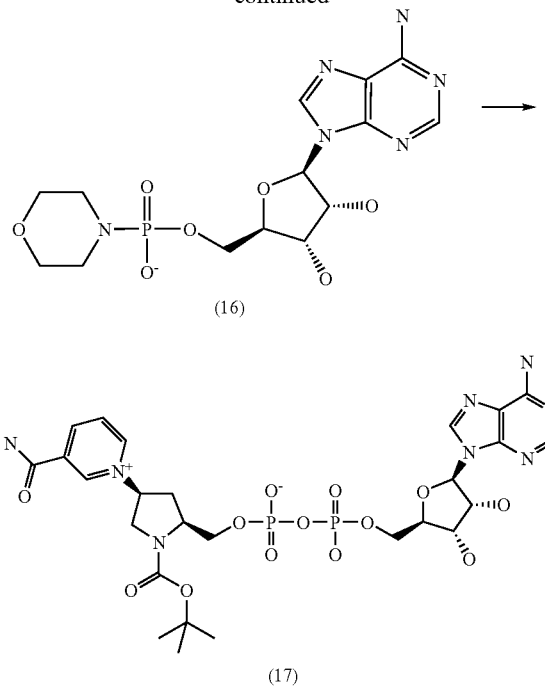

A mixture of AMP morpholidate (compound 16 from stage 7a) (2.53 g, 3.61 mmol), compound 15 from stage 6 (1.60 g, 3.98 mmol), MnCl$_2$ solution in formamide 0.2 M* (27.1 ml, 5.42 mmol) and anhydrous MgSO$_4$ (0.87 g, 7.95 mmol) were stirred overnight at room temperature and after this time were largely converted as determined by TLC (RP8 MeOH/W 9/1). The reaction mixture was precipitated with acetonitrile and suction filtered.

Residue=5.3 g (theoretical yield 2.64 g)**

MS ESI ES−729.3=product, ES−415=cation of AMP morpholidate, ES−400.2/ES+402.1 residues of compound 15 (stage 6)

TLC RP 8 F254 Rf 0.085

* In order to prepare this solution 2516 mg anhydrous MnCl$_2$ was dissolved in 100 ml 99.99% formamide while stirring and subsequently 4A molecular sieve was added.

** The residue was further processed as a crude product.

VIII. Synthesis of pNAD 8th Stage (Compound 18, Pyrrolidinyl-NAD)

5.0 ml trifluoroacetic acid (TEA) was added to 500 mg compound 17 from stage 7 (crude product, contains about 50% salts) and stirred for 1 h at room temperature and subsequently concentrated by evaporation. 500 ml colourless oil was formed as the residue MS ESI ES− 729.24 (addition of NH$_3$ necessary)

2 Portions of 200 mg and 300 mg were each purified in 2 separation steps:

First Separation Step:

Fractogel EMD SO3-s column: D (inner)=14 mm L (packing)=85 mm

I. Conditioning (flow rate 5 ml/min)
a) 100 ml H$_2$O
b) 200 ml 0.25 M H$_2$SO$_4$
c) 100 ml H$_2$O
d) 200 ml 1 M ammonia solution
e) 100 ml H$_2$O II. Separation:
a) apply 200 ml substance dissolved in 5 ml H$_2$O
b) elute with a gradient of H$_2$O→0.2 M NH$_4$HCO$_3$ solution, (mobile solvent A=250 ml H$_2$O submitted in an Erlenmeyer flask and stirred on a magnetic stirrer, pumped onto the column at a rate of 5 ml/min mobile solvent B=0.2 M NH$_4$HCO$_3$ solution pumped at 2.5 ml/min to A).

III. Fractionation:
a) fractions each of 3 ml
b) 1st peak impurities
c) 2nd peak after about 70 ml preliminary eluate=substance IV. Reconditioning:
a) 100 ml 1 M ammonium solution
b) 100 ml H$_2$O 2nd Separation Step:

Diaion HP20, column D (inner)=30 mm L (packing) 130 mm eluted with 100 ml H$_2$O and 100 ml H$_2$O/5% isopropanol.

The substance already elutes with the water phase; only impurities are present in the isopropanol fraction.

3 fractions were obtained according to analytical HPLC:
F1=13.5 mg
F2=5.5 mg
F3=11.5 mg
Total=30.5 mg=12.2%

The identity of the pyrrolidinyl NAD (compound 18) was confirmed by NMR analyses.

Glucose Dehydrogenase Assay for pNAD

In order to examine the role of pNAD as a cofactor for glucose dehydrogenase (GlucDH), a glucoseDH activity assay in 0.1 M Tris/0.2 M NaCl (pH 8.5) buffer was carried

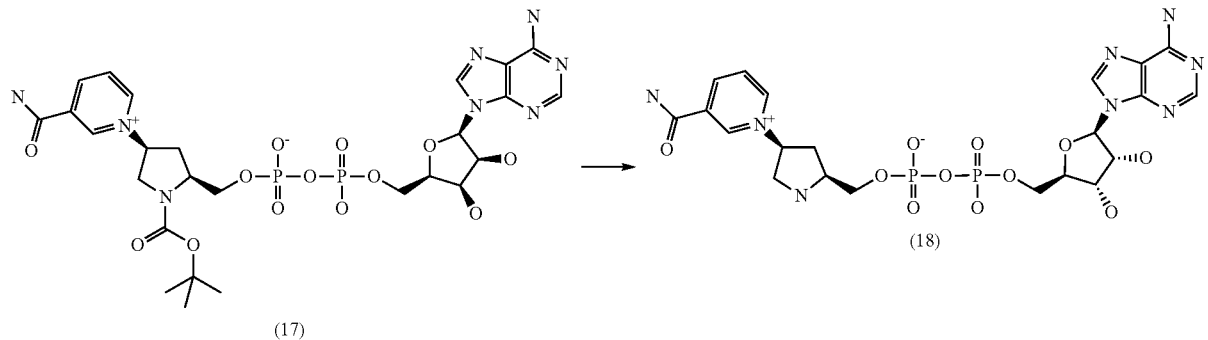 [SMILES: CC(C)(C)OC(=O)N1C[C@@H]([n+]2cccc(C(N)=O)c2)C[C@H]1COP(=O)([O-])OP(=O)(O)OC[C@H]1O[C@@H](n2cnc3c(N)ncnc32)[C@@H](O)[C@H]1O ; NC(=O)c1ccc[n+]([C@@H]2CN[C@H](COP(=O)([O-])OP(=O)(O)OC[C@H]3O[C@@H](n4cnc5c(N)ncnc54)[C@H](O)[C@@H]3O)C2)c1]

out. The concentration of glucose was 80 mM. pNAD and NAD concentrations of 0.05-0.5 mM were used. To this, 10 mg/ml (pNAD) or 0.002 mg/ml (NAD) [83 or 0.017 μM respectively] GlucDH was added. The assay was carried out at room temperature and the enzymatic reaction was monitored by recording absorption spectra at regular time intervals. The values shown in table 1 refer to an absorption measurement after 4 min.

TABLE 1

| (p)NAD (mM) | U/ml | % activity | [GlucDH] used |
|---|---|---|---|
| 0.05 NAD | 539 | 100 | 0.02 mg/ml |
| 0.4 NAD | 1556 | 100 | 0.002 mg/ml |
| 0.05 pNAD | 0.00017 | 0.00003 | 10 μL 10 mg/ml |
| 0.4 pNAD | 0.0024 | 0.00015 | 10 μL 10 mg/ml |

Absorption Spectra of pNAD and pNADH

Figure 6A:
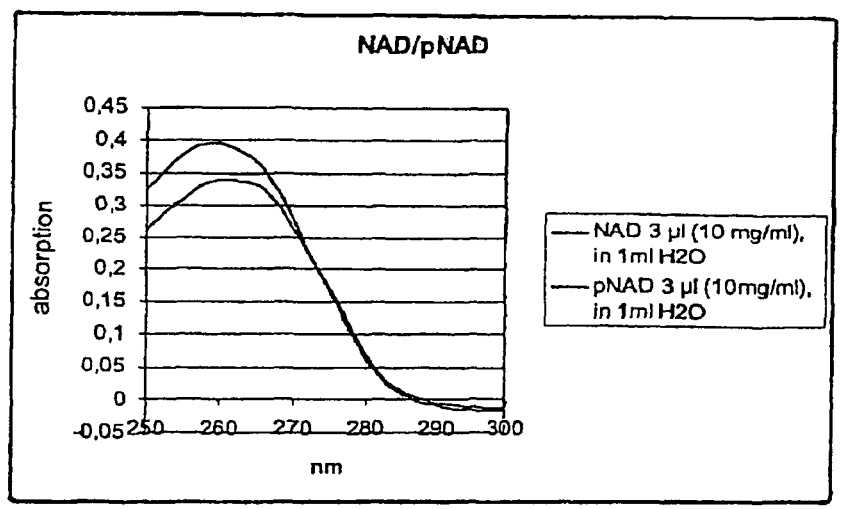
FIG. 6A shows absorption spectra of NAD and pNAD.
Figure 6B:
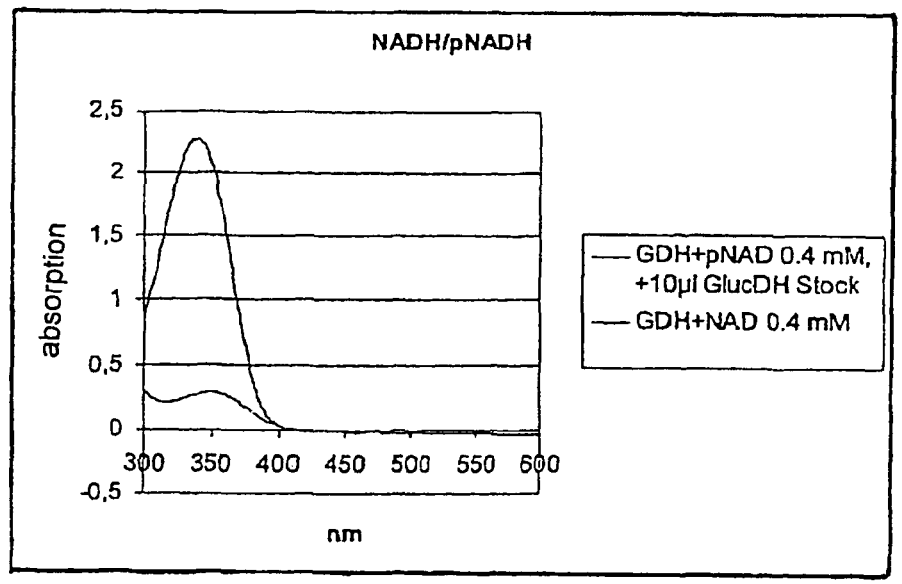
FIG. 6B shows absorption spectra of NADH and/or pNADH.

Absorption, spectra of NAD and pNAD and/or NADH and pNADH are shown in FIGS. 6A and 6B. NAD and pNAD exhibit an absorption maximum at 260 nm. pNADH i.e. pNAD after the GlucDH activity assay exhibits a red shift of the absorption maximum by about 10 nm (FIG. 6B) compared to NADH.

Figure 7:
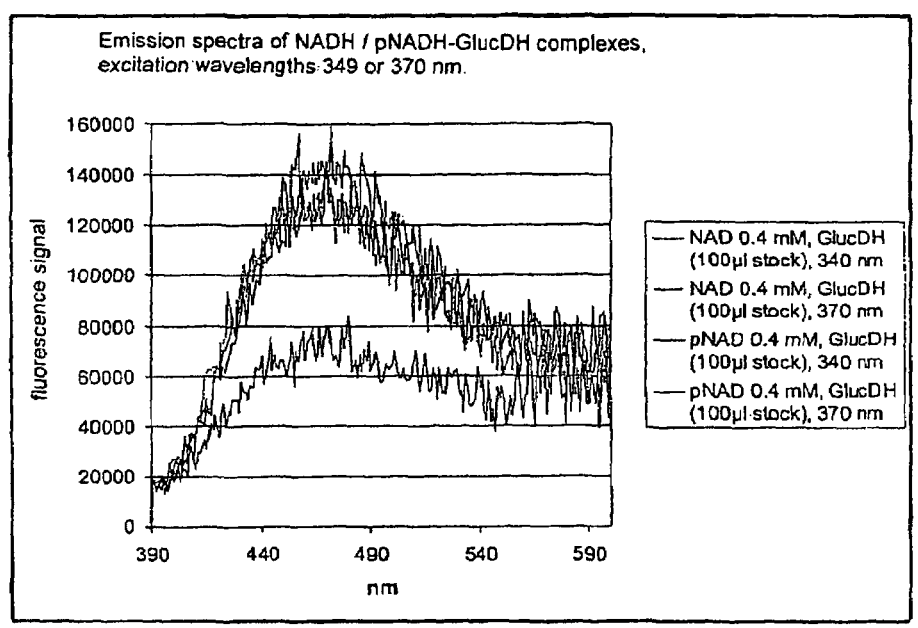
FIG. 7 shows fluorescence spectra of NADH and pNADH as a GlucDH complex (emission spectra).
Figure 8:
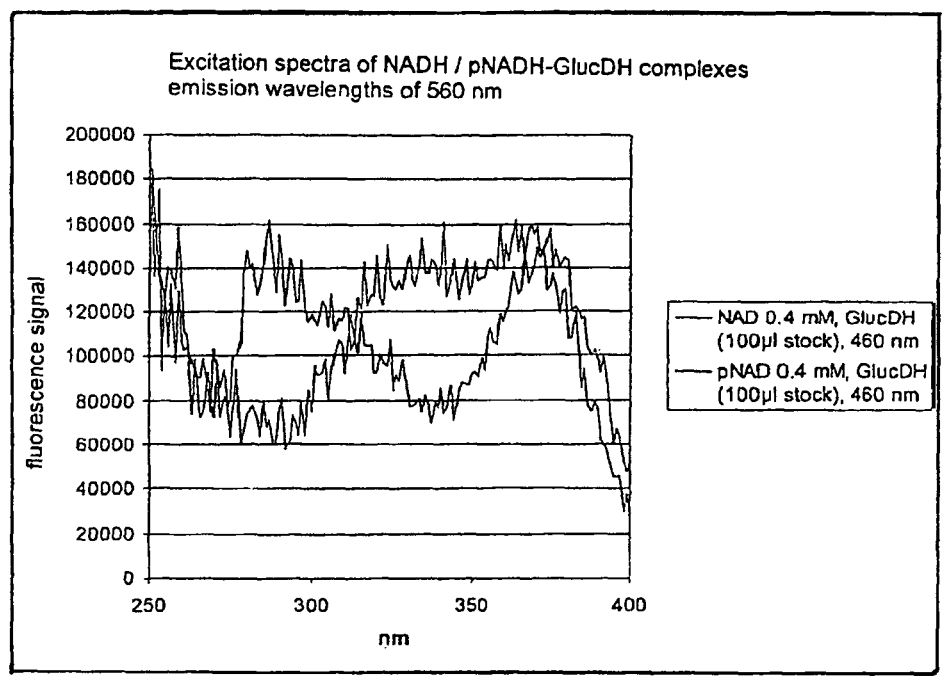
FIG. 8 shows fluorescence spectra of NADH and pNADH as a GlucDH complex (excitation spectra).

Fluorescence spectra of NADH and pNADH as GlucDH complexes are additionally shown in FIGS. 7 and 8. The spectra were in each case recorded after the GlucDH activity assay. FIG. 7 shows emission spectra of NADH/pNADH-GlucDH complexes at excitation wavelengths of 340 and 370 nm. The emission spectra of NADH and pNADH at 370 nm excitation wavelength are similar. FIG. 8 shows an excitation spectrum for an NADH/pNADH-GlucDH complex at an emission, wavelength of 460 nm. pNADH exhibits a broader excitation spectrum than NADH. The spectra were also recorded after GlucDH activity assays.

Investigation of the Stability of pNAD

Figure 9:
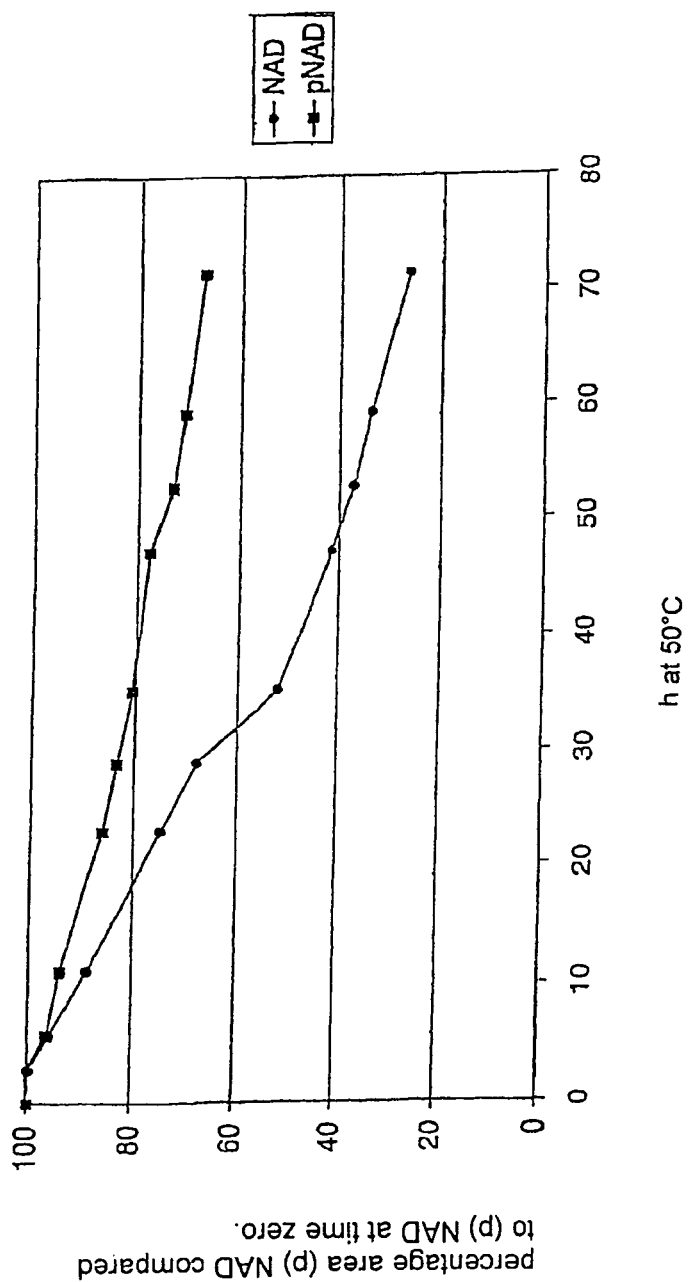
FIG. 9 illustrates a comparison of the stability of NAD and pNAD.

In order to examine the stability of pNAD compared to NAD, the same amounts of NAD and pNAD were each taken up in 0.15 M $KPO_4$, 1 M NaCl buffer (pH 7.0) and incubated at 50° C. The decomposition of NAD and/or pNAD were monitored by HPLC. FIG. 9 shows the percentage areas of the (p)NAD amounts compared to the (p)NAD amounts at time zero. The figure shows that pNAD is very stable compared to NAD.

C) Preparation of carbaNAD Cyclophosphate (19)

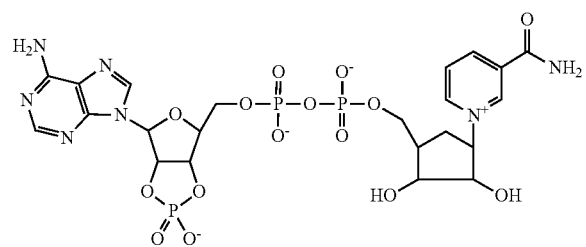 [SMILES: NC(=O)c1ccc[n+](C2CC(COP(=O)([O-])OP(=O)([O-])OCC3OC(n4cnc5c(N)ncnc54)C4OP(=O)([O-])OC34)C(O)C2O)c1]

79 mg (0.1 mmol) O5'-(hydroxy-morpholin-phosphoryl)-$O_2'$,$O_3'$-hydroxy-phosphoryl-adenosine, N-cyclohexyl-morpholine-4-carbonimidic acid cyclohexylamine salt dihydrate (dried by coevaporation with pyridine (Morphat et al., J. Am. Chem. Soc. 83; 1961; 663-675), 44 mg (0.105 mmol) carbaNMN monophosphate and subsequently 25 mg dry magnesium sulfate were added to 0.74 ml of a 0.2 manganese chloride solution in absolute formamide. The mixture was stirred under argon for three days in a closed reaction vessel and subsequently added to 10 ml acetonitrile while stirring. The precipitate was removed by filtration, purified by RP chromatography on a RP 18 Hypersil ODS, 250×21.2 mM, 5 μm column using a 0% B to 100% B gradient for 60 min: Eluant A: 0.1 M triethylammonium acetate, eluant B: 1:4 mixture of 0.1 M triethylammonium acetate and acetonitrile, flow rate: 10 ml/min. The elution was monitored by detection at 2.60 nm. The main fraction was collected and lyophilized 5 times in order to remove the triethylammonium acetate. The triethylammonium salt was converted into the free acid with Dowex 50 WX2 and subsequently into the lithium salt. Yield: 10 mg.

D) Preparation of carbaNADP (20)

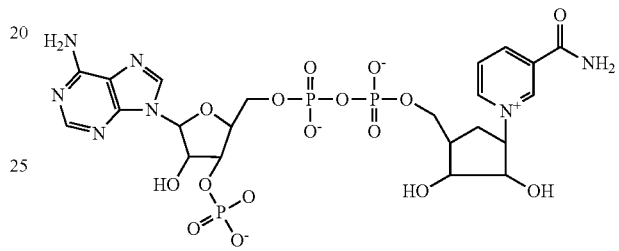

Three times four units ribonuclease T2 were added within 6 h at 37° C. to a solution of 2.2 mg carbaNAD cyclophosphate lithium salt (19) in 1 ml Bis-tris-propane buffer (0.02 M, pH 7.5). The mixture was kept overnight at 37° C. The enzyme was denatured by heating to 65° C. for 20 min. After filtration a purification was carried out by RP chromatography on a RP 18 Hypersil ODS, 250×21.2 mm, 5 μm column using a gradient of 0% B to 100% B for 60 min. Eluant A: 0.1 M triethylammonium acetate; eluant B: 1:4 mixture of 0.1 ml triethylammonium acetate and acetonitrile; flow rate: 10 ml/mm. The elution was monitored by detection at 260 nm. The main fraction was collected and lyophilized 5 times in order to remove the triethyl-ammonium acetate.

Mass spectrum (MALDI Applied Biosystems Voyager System 6327: calculated 742.45, found: 743.17).

E) Glucose Dehydrogenase Activity Assay for cNAD

A glucose dehydrogenase activity assay for cNAD compared to NAD was carried out as described under B) for pNAD. For this purpose glucose dehydrogenase concentrations of 0.1 (cNAD) and 0.002 mg/ml (NAD) [0.83 and 0.017 μM respectively] were used. The amounts used and the results are shown in table 2.

TABLE 2

| (c)NAD (mM) | U/ml | % Activity | [GlucDH] used |
|---|---|---|---|
| 0.05 NAD | 430 | 100 | 0.002 mg/ml |
| 0.1 NAD | 556 | 100 | 0.002 mg/ml |
| 0.05 cNAD | 2.7 | 0.63 | 0.1 mg/ml |
| 0.1 cNAD | 5.3 | 0.95 | 0.1 mg/ml |

F) Absorption Spectra of cNAD and cNADH

Figure 10A:
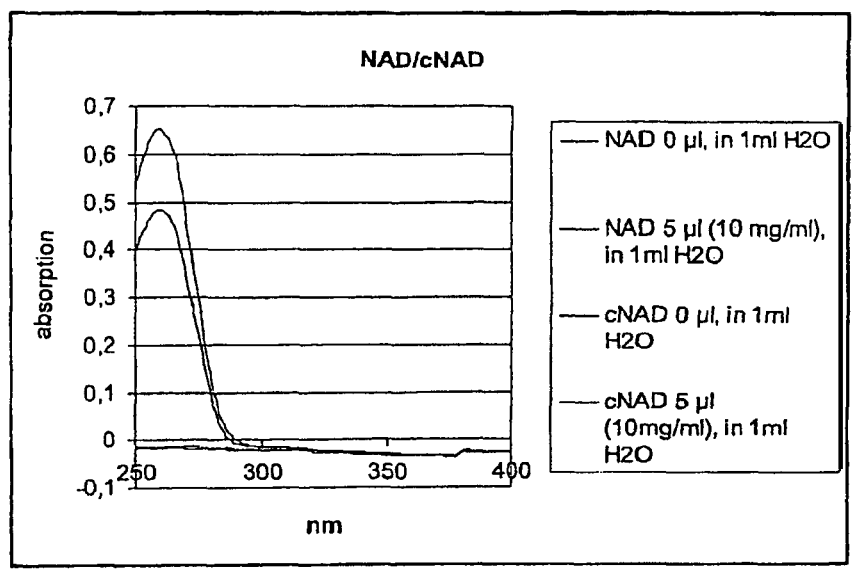
FIG. 10A shows absorption spectra of NAD and cNAD.
Figure 10B:
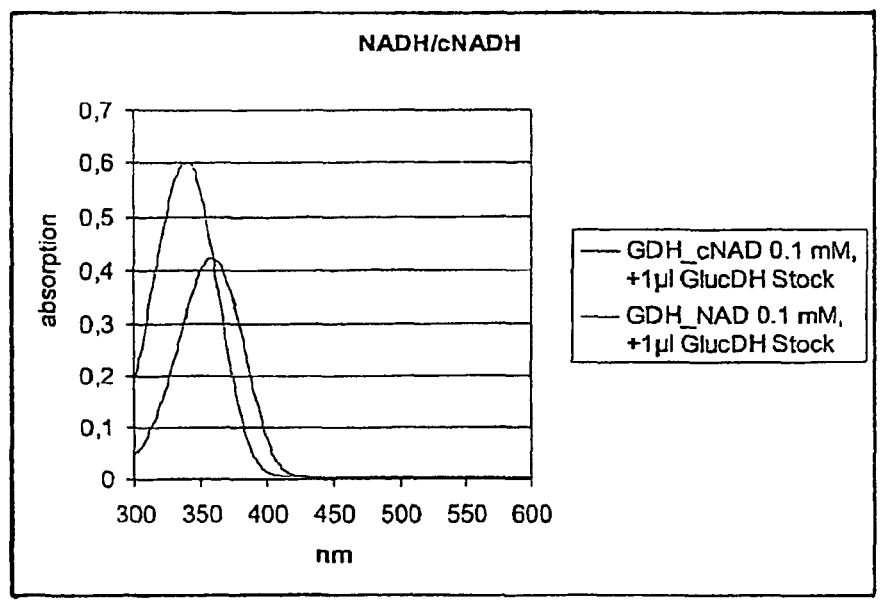
FIGS. 10B and 10C show absorption spectra of NADH and/or cNADH.
Figure 10C:
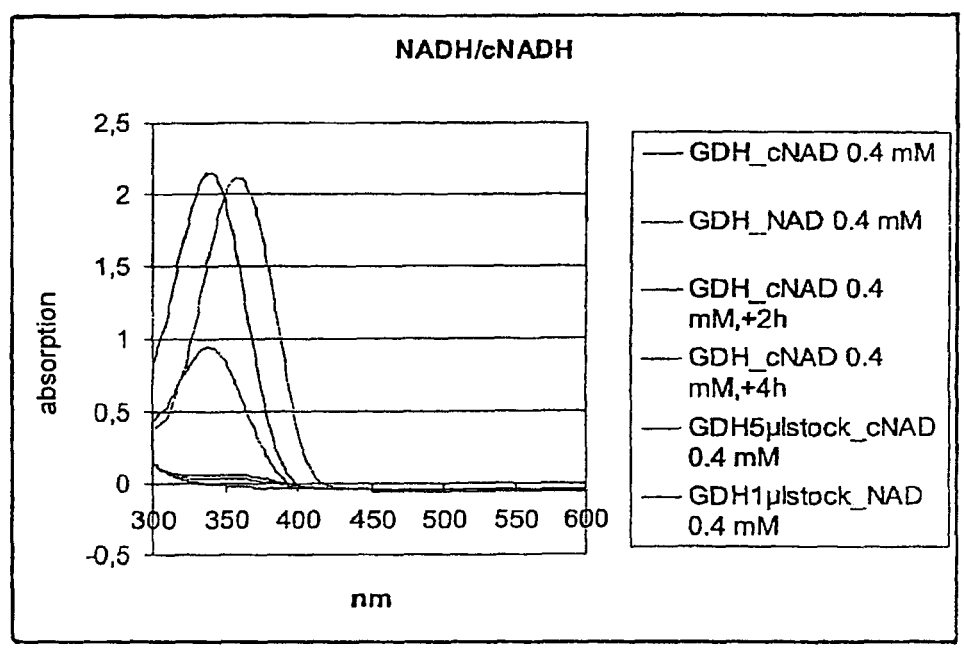

FIGS. 10A, 10B and 10C show absorption spectra of NAD and cNAD. NAD as well as cNAD have an absorption maximum at 260 nm. FIG. 10B shows absorption spectra of NADH and cNADH where the spectra were in each case recorded after a glucose dehydrogenase activity assay. The absorption maximum of cNADH exhibits a red shift of 20 nm. Further absorption spectra for NADH and cNADH are shown in FIG. 10C in which different conditions for the associated glucose dehydrogenase activity assay were selected as stated in the legends.

Figure 11:
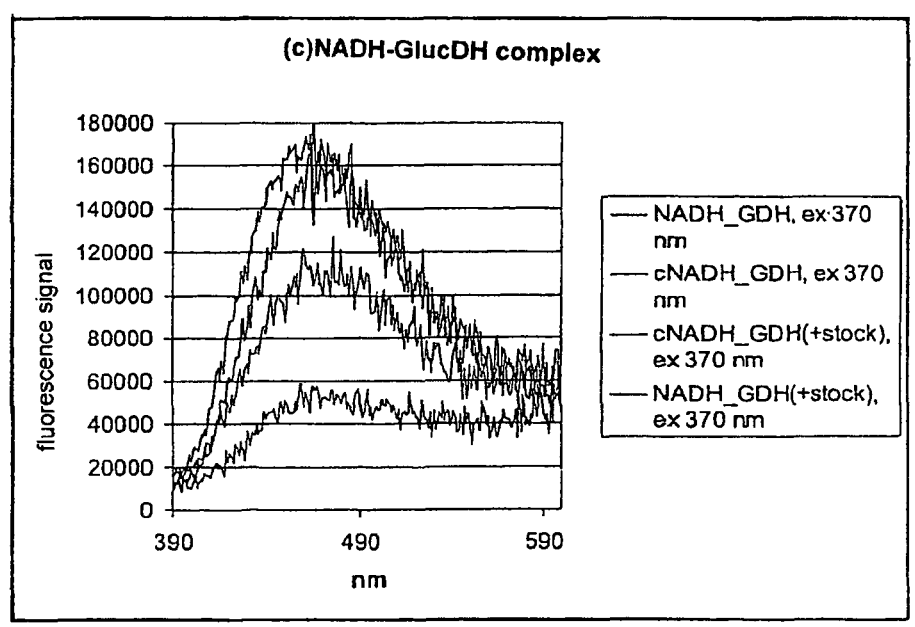
FIG. 11 shows fluorescence spectra of NADH and cNADH as a GlucDH complex.

FIG. 11 additionally shows fluorescence spectra of NADH and cNADH as GlucDH complexes. The spectra were recorded at an excitation wavelength of 370 nm after a glucose dehydrogenase activity assay. NADH as well as cNADH exhibit an increase of the fluorescence signal when treated with GlucDH.

The features disclosed in the above description, the claims and the drawings may be important both individually and in any combination with one another for implementing the present invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison:, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A test element configured for determining glucose, comprising (i) a coenzyme-dependent enzyme comprising glucose dehydrogenase or a substrate for such an enzyme and (ii) a compound of the following general formula (I) as the coenzyme:

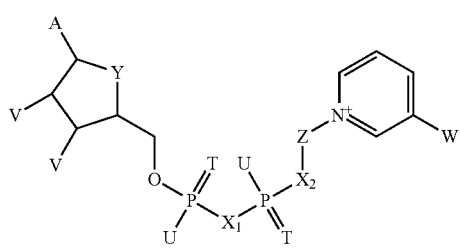

(I)

in which
A=adenine or an analogue thereof,
T=in each case independently denotes O, S,
U=in each case independently denotes OH, SH, $BH_3^-$, $BCNH_2^-$,
V=in each case independently denotes OH or a phosphate group,
W=COOR, $CON(R)_2$, COR, $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, $NCH_3$,
Y=NH, S, O, $CH_2$,
Z=a residue comprising a cyclic group with 5 C atoms which optionally contains a heteroatom selected from O, S and N
and optionally one or more substituents, and a residue $CR4_2$
wherein $CR4_2$ is bound to the cyclic group and to $X_2$,
where R4=in each case independently denotes H, F, Cl, $CH_3$,
provided that Z and the pyridine residue are not linked by a glycosidic bond,
or a salt or optionally a reduced form thereof.

2. The test element according to claim 1, wherein the substituents on Z are selected from the group consisting of OH, F, Cl and $C_1$-$C_2$-alkyl which is optionally fluorinated or chlorinated or/and OH-substituted, O—$C_1$-$C_2$-alkyl.

3. The test element according to claim 1, comprising a compound of the following formula (I') as the coenzyme:

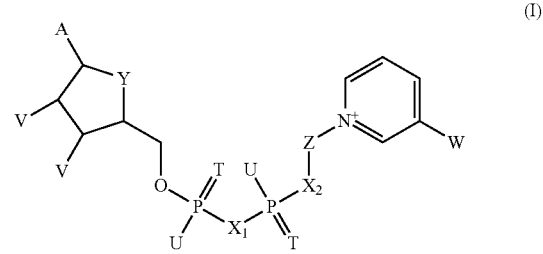

(I)

in which
A=adenine or an analogue thereof,
T=in each case independently denotes O, S,
U=in each case independently denotes OH, SH, $BH_3^-$, $BCNH_2^-$,
V=in each case independently denotes OH or a phosphate group,
W=COOR, $CON(R)_2$, COR, $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, $NCH_3$,
Y=NH, S, O, $CH_2$,
Z=a saturated or unsaturated carbocyclic or heterocyclic five-membered ring of the general formula (II)

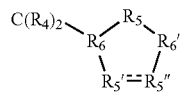

(II)

in which a single or double bond can be present between R5' and R5", in which
R4=in each case independently denotes H, F, Cl, $CH_3$,
R5=$CR4_2$,
if a single bond is present between R5' and R5", then R5'=O, S, NH, $NC_1$-$C_2$-alkyl, $CR4_2$, CHOH, $CHOCH_3$, R5"=$CR4_2$, CHOH, $CHOCH_3$,
if a double bond is present between R5' and R5", then R5'=R5"=CR4,
R6, R6'=in each case independently denote CH, $CCH_3$
or a salt or optionally a reduced form thereof.

4. The test element according to claim 1, wherein W=CONH$_2$ or COCH$_3$.

5. The test element according to claim 1, wherein the test element comprises a test strip configured for carrying the enzyme and coenzyme.

6. A method of determining an analyte comprising the steps of (a) providing a test element according to claim 1; (b) contacting the test element with a sample; (c) measuring a value relating to a change in one of the enzyme and coenzyme; and (d) correlating the value to a concentration of the analyte, wherein the analyte is at least one of the analytes selected from the group consisting of glucose, lactic acid, malic acid, glycerol, alcohol, cholesterol, triglycerides, ascorbic acid, cysteine, glutathione, peptides, urea, ammonium, salicylate, pyruvate, 5'-nucleotidase, creatine kinase (CK), lactate dehydrogenase (LDH) and carbon dioxide.

7. The test element according to claim 1, wherein
A=adenine,
T=in each case denotes O,
U=in each case denotes OH,
V=in each case denotes OH,
W=CON(R)$_2$ in which R denotes H,
X$_1$=O,
X$_2$=O,
Y=O, and
Z=a saturated carbocyclic 5-membered ring of the general formula (II)

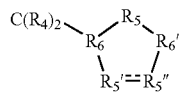
(II)

in which a single bond is present between R5' and R5", and in which
R4=H,
R5=CR4$_2$,
R5'=CHOH,
R5"=CHOH,
R6=CH, and
R6'=CH.

8. The test element according to claim 1, the test element being configured for determining glucose in a sample comprising one of a body fluid, waste water, and food.

9. The test element according to claim 1, the test element being in the form of a dry test wherein the enzyme or substrate for such enzyme and the compound are provided as a swellable or absorbent material that is wetted by a sample liquid for determining glucose.

10. A compound of the general formula (I"):

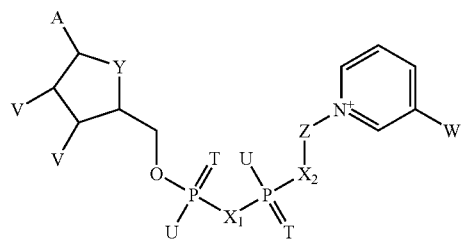
(I")

in which
A=adenine or an analogue thereof,
T=in each case independently denotes O, S,
U=in each case independently denotes OH, SH, BH$_3^-$, BCNH$_2^-$, V=in each case independently denotes OH or a phosphate group,
W=COOR, CON(R)$_2$, COR, CSN(R)$_2$ in which R in each case independently denotes H or C$_1$-C$_2$-alkyl,
X$_1$, X$_2$=in each case independently denote O, or NH,
Y=NH, S, O, CH$_2$,
Z=a saturated or unsaturated carbocyclic or heterocyclic five-membered ring of the general formula (II)

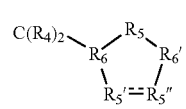
(II)

in which a single or double bond can be present between R5' and R5",
R4=in each case independently denotes H, F, Cl, CH$_3$,
R5=CR4$_2$,
if a single bond is present between R5' and R5", then R5'=O, S, NH, NC$_1$-C$_2$-alkyl, CR4$_2$, CHOH, CHOCH$_3$, R5"=CR4$_2$, CHOH, CHOCH$_3$,
if a double bond is present between R5' and R5", then R5'=R5"=CR4,
R6, R6'=in each case independently denote CH, CCH$_3$
provided that if R5=CH$_2$, T=O, U=in each case OH, V=OH, W=CONH$_2$, X$_1$, X$_2$=O and Y=O, then R5' and R5" are not simultaneously CHOH,
or a salt or optionally a reduced form thereof.

11. The compound according to claim 10, wherein at least one residue U is different from OH.

12. The compound according to claim 11, wherein at least one residue U=BH$_3^-$.

13. The compound according to claim 10, wherein W=CONH$_2$ or COCH$_3$.

14. The compound according to claim 10, wherein a first residue V is an OH group and a second residue V is a phosphate group, and wherein the OH group and the phosphate group are able to form a cycle with the carbon atoms to which they are bound.

15. The compound according to claim 10, wherein R5'=CR4$_2$ or CHOH.

16. The compound according to claim 10, wherein R5' is O.

17. The compound according to claim 10, wherein R5'=NH or NC$_1$-C$_2$-alkyl.

18. An enzyme-coenzyme complex comprising a compound according to claim 10 in combination with a suitable enzyme.

19. The complex according to claim 18, wherein the enzyme is a dehydrogenase selected from the group consisting of glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1.1.6), alcohol dehydrogenase (E.C.1.1.1.1), alpha-hydroxybutyrate dehydrogenase, sorbitol dehydrogenase, and an amino acid dehydrogenase comprising L-amino acid dehydrogenase (E.C.1.4.1.5).

20. A method for detecting an analyte in a fluid sample comprising the steps of (a) providing a test element, the test element carrying a compound according to claim 10 and an enzyme; and (b) analyzing an enzymatic reaction involving the analyte and correlating a change in the compound or the enzyme to a quantity of the analyte.

21. A reagent kit comprising in combination a compound according to claim 10, a suitable enzyme, and a suitable reaction buffer.

22. The reagent kit according to claim 21, wherein the enzyme is a dehydrogenase selected from the group consisting of glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1.1.6), alcohol dehydrogenase (E.C.1.1.1.1), alpha-hydroxybutyrate dehydrogenase, sorbitol dehydrogenase, and an amino acid dehydrogenase comprising L-amino acid dehydrogenase (E.C.1.4.1.5).

23. A method for detecting an analyte comprising the steps of:
  (a) contacting a sample with a reagent kit according to claim 21; and
  (b) detecting the analyte.

24. The method according to claim 23, wherein the analyte is detected photometrically or fluorometrically.

25. The compound according to claim 10, wherein the compound comprises carbaNADP or a salt or a reduced form thereof.

* * * * *